(12) United States Patent
Vayser et al.

(10) Patent No.: US 10,456,190 B2
(45) Date of Patent: Oct. 29, 2019

(54) METHODS AND APPARATUS FOR ELECTROSURGICAL ILLUMINATION AND SENSING

(71) Applicant: Invuity, Inc., San Francisco, CA (US)

(72) Inventors: Alex Vayser, Mission Viejo, CA (US); Fernando Erismann, New York, NY (US); Scott Taylor, San Martin, CA (US); Jason Hegener, San Francisco, CA (US)

(73) Assignee: Invuity, Inc., San Francisco, CA (US)

( * ) Notice: Subject to any disclaimer, the term of this patent is extended or adjusted under 35 U.S.C. 154(b) by 480 days.

(21) Appl. No.: 14/962,942

(22) Filed: Dec. 8, 2015

(65) Prior Publication Data

US 2016/0157920 A1    Jun. 9, 2016

Related U.S. Application Data

(60) Provisional application No. 62/089,023, filed on Dec. 8, 2014, provisional application No. 62/136,335, filed
(Continued)

(51) Int. Cl.
*A61B 18/14* (2006.01)
*A61B 90/30* (2016.01)
(Continued)

(52) U.S. Cl.
CPC .......... *A61B 18/1402* (2013.01); *A61B 90/30* (2016.02); *A61B 5/0075* (2013.01); *A61B 5/01* (2013.01); *A61B 5/0538* (2013.01); *A61B 5/6847* (2013.01); *A61B 5/6886* (2013.01); *A61B 18/1477* (2013.01);
(Continued)

(58) Field of Classification Search
CPC ....... A61B 90/30; A61B 18/18; A61B 90/306; A61B 17/3476; A61B 2018/00589; A61B 2018/00607
See application file for complete search history.

(56) References Cited

U.S. PATENT DOCUMENTS 3,677,262 A    7/1972    Zukowski
4,562,838 A *  1/1986    Walker ............... A61B 18/1402
                                              219/230
(Continued)

FOREIGN PATENT DOCUMENTS

WO    WO-9510981 A1    4/1995
WO    WO-2011127902 A1    10/2011
(Continued)

OTHER PUBLICATIONS

International search report and written report dated Feb. 12, 2016 for PCT/US2015/064553.
"EP15866893 Extended Search Report dated Jun. 4, 2018.".

*Primary Examiner* — David W Bates
(74) *Attorney, Agent, or Firm* — McDonnell Boehnen Hulbert & Berghoff LLP

(57) ABSTRACT

An illuminated energy device includes a handle, an optical waveguide coupled to the handle, and an energy tip such as an electrode coupled to the optical waveguide. The optical waveguide is preferably adjustably coupled to the handle, and adjustment of the optical waveguide moves a distal end of the optical waveguide closer to or further away from a target such as tissue in a surgical field.

33 Claims, 28 Drawing Sheets

Related U.S. Application Data on Mar. 20, 2015, provisional application No. 62/212,516, filed on Aug. 31, 2015.

(51) Int. Cl.

| | |
|---|---|
| *A61B 18/00* | (2006.01) |
| *A61B 5/00* | (2006.01) |
| *A61B 5/01* | (2006.01) |
| *A61B 5/053* | (2006.01) |
| *A61B 18/20* | (2006.01) |

(52) U.S. Cl.
CPC .............. *A61B 2018/00017* (2013.01); *A61B 2018/00589* (2013.01); *A61B 2018/00607* (2013.01); *A61B 2018/00797* (2013.01); *A61B 2018/00922* (2013.01); *A61B 2018/00982* (2013.01); *A61B 2018/1412* (2013.01); *A61B 2018/2005* (2013.01); *A61B 2090/306* (2016.02); *A61B 2090/309* (2016.02); *A61B 2218/008* (2013.01)

(56) References Cited

U.S. PATENT DOCUMENTS

| | | | |
|---|---|---|---|
| 4,688,569 | A | 8/1987 | Rabinowitz |
| 5,221,279 | A | 6/1993 | Cook et al. |
| 6,550,926 | B2 | 4/2003 | Berger |
| 6,610,057 | B1 | 8/2003 | Ellman et al. |
| 7,083,601 | B1 | 8/2006 | Cosmescu |
| 8,690,872 | B2 | 4/2014 | Jayaraj |
| 8,882,767 | B2 | 11/2014 | Greep et al. |
| 8,882,768 | B2 | 11/2014 | Greep et al. |
| 9,237,922 | B2 | 1/2016 | Bromley et al. |
| 9,259,260 | B2 | 2/2016 | Greep et al. |
| 9,289,261 | B2 | 3/2016 | Shvetsov et al. |
| 9,375,253 | B2 | 6/2016 | Greep et al. |
| D761,962 | S | 7/2016 | Fleenor |
| 10,194,975 | B1 * | 2/2019 | Hubelbank .............. A61B 18/14 |
| 2002/0009275 | A1 | 1/2002 | Williams et al. |
| 2003/0012531 | A1 * | 1/2003 | Nechitailo ............ G02B 6/4411 |
| | | | 385/114 |
| 2004/0097910 | A1 * | 5/2004 | Brugger ................ A61B 18/201 |
| | | | 606/10 |
| 2005/0283148 | A1 | 12/2005 | Janssen et al. |
| 2007/0208226 | A1 | 9/2007 | Grey et al. |
| 2010/0145333 | A1 | 6/2010 | Dethier et al. |
| 2011/0060332 | A1 | 3/2011 | Cheng |
| 2011/0190768 | A1 | 8/2011 | Shvetsov et al. |
| 2012/0265184 | A1 * | 10/2012 | Sliwa .................... A61B 5/0084 |
| | | | 606/15 |
| 2012/0283728 | A1 * | 11/2012 | Cosmescu .............. A61B 90/35 |
| | | | 606/46 |
| 2013/0021783 | A1 * | 1/2013 | Vanko ...................... B25F 5/021 |
| | | | 362/119 |
| 2013/0267786 | A1 | 10/2013 | Vayser et al. |
| 2013/0343046 | A1 * | 12/2013 | Tsai .......................... F21K 9/00 |
| | | | 362/217.05 |
| 2014/0088371 | A1 * | 3/2014 | Vayser ............... A61B 1/00135 |
| | | | 600/249 |
| 2014/0221763 | A1 | 8/2014 | Vayser et al. |
| 2014/0276763 | A1 | 9/2014 | Greep et al. |
| 2014/0293590 | A1 | 10/2014 | Pathy |
| 2014/0303449 | A1 * | 10/2014 | Balog ................. A61B 18/1402 |
| | | | 600/249 |
| 2015/0216618 | A1 * | 8/2015 | Jayaraj ................... A61B 90/13 |
| | | | 600/249 |
| 2019/0015147 | A1 * | 1/2019 | Hubelbank ............ A61B 18/14 |

FOREIGN PATENT DOCUMENTS

| | | |
|---|---|---|
| WO | WO-2012118746 A2 | 9/2012 |
| WO | WO-2014093664 A1 | 6/2014 |
| WO | WO-2014165551 A1 | 10/2014 |
| WO | WO-2015085108 A1 | 6/2015 |
| WO | WO-2016196562 A1 | 12/2016 |

\* cited by examiner

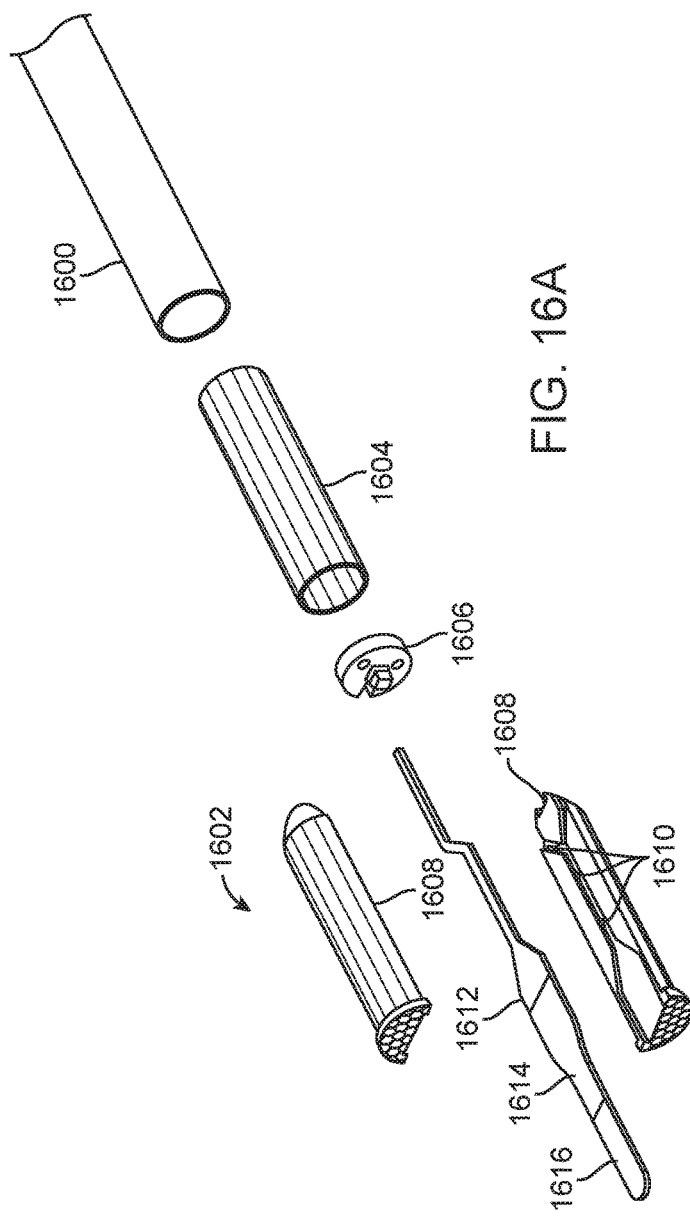
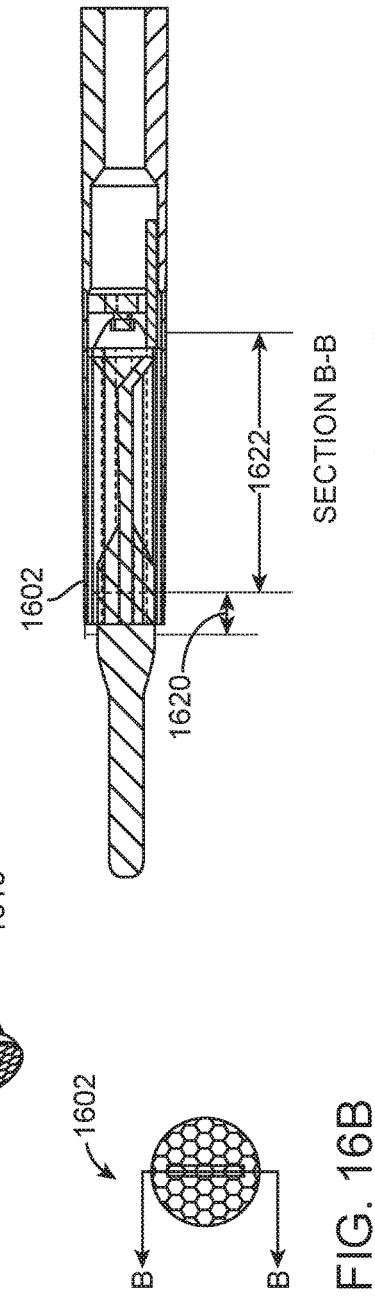
FIG. 16A
FIG. 16B
FIG. 16C

METHODS AND APPARATUS FOR ELECTROSURGICAL ILLUMINATION AND SENSING

CROSS-REFERENCE TO RELATED APPLICATIONS

The present application is a non-provisional of, and claims the benefit of U.S. Provisional Patent Application Nos. 62/089,023 filed Dec. 8, 2014; 62/136,335 filed Mar. 20, 2015; and 62/212,516 filed Aug. 31, 2015; the entire contents of which are incorporated herein by reference.

BACKGROUND OF THE INVENTION

Field of the Invention

The present application generally relates to medical devices, systems and methods, and more particularly relates to illuminated electrosurgical instruments such as illuminated energy tips such as electrosurgical, plasma, or laser tips. Conventional electrosurgical tools are commonly used in most surgical procedures. Energy hand-pieces generally include a hand-piece (also referred to herein as a handle) and an energy tip. The hand-piece is ergonomically shaped to allow a surgeon to manipulate the hand-piece during surgery and position the energy tip into a desired position where energy, typically radiofrequency (RF) energy is delivered to target tissue to cut or coagulate the tissue. One of the challenges with these devices, is that they are often used in deep dark openings which are difficult to access without obstructing the surgical field, and which are difficult to adequately illuminate. Commercially available energy hand-pieces do not always include a lighting element for illuminating the surgical field and thus lighting must be supplied by another device such as a headlamp that the surgeon wears or an overhead light that is manually adjusted. The hand-pieces that do provide illumination may have illumination elements such as light emitting diodes (LEDs) that are mounted releasably or fixedly into the handle of the device, but this is not necessarily the optimal position or distance from the work surface or target, and these devices may not have optimized lensing for collecting and shaping the light, and advanced light shaping may require larger profile lenses that are not practical for a surgical application with limited profile. Light shaping is also critical as conventional LED dye have a broad Lambertian output that require collection and directionality. High powered LEDs also generate significant amount of heat from the LED dye and the heat may be conducted to the core of the LED board. Therefore, cooling is required in order to keep the entire device safe, especially when in contact with a patient. Also, it would be desirable to keep the light as close to the surgical target as possible thereby ensuring sufficient brightness and intensity. Many commercially available devices have LEDs positioned at the very distal tip of the device but this can result in challenges with lighting quality such as sufficient brightness, device profile, beam directionality as well as light shaping and thermal management. Therefore, the light provided by the LEDs is preferably thermally safe, low profile and directed and shaped for optimal illumination of the surgical target. It would therefore be desirable to provide improved energy hand-pieces that provide better lighting in order to illuminate a work surface or target area such as a surgical field. At least some of these objectives will be met by the embodiments disclosed below.

SUMMARY OF THE INVENTION

The present invention generally relates to medical systems, devices and methods, and more particularly relates to illuminated energy devices, systems and methods.

The illuminated energy devices may optionally include a waveguide to help deliver light to a target work area. Preferably, the waveguide is a light conducting, non-fiber optic, optical element where the light passing therethrough has at least one internal reflection.

In a first aspect of the present invention, an illuminated energy device comprises a handle, an optical waveguide coupled to the handle, and an energy tip coupled to the optical waveguide. The energy tip may be adjustably coupled to the waveguide or the handle, and adjustment of the optical waveguide may move the distal end closer to or further away from a target such as a tissue target in a surgical field. The energy tip may be an electrode and may be removably coupled with the optical waveguide or the handle. The optical waveguide may be independently movable relative to the energy tip.

In another aspect of the present invention, a method for illuminating a surgical target comprises providing an optical waveguide coupled to an energy tip such as an electrode, illuminating the surgical field with light from the optical waveguide, and moving the optical waveguide and energy tip together or independently of one another, toward or away from the surgical target. This adjusts the length of the energy tip and the optical waveguide and may adjust illumination of the target such as target tissue in a surgical field if the waveguide moves independently of the tip. The method may further comprise replacing the energy tip with a different energy tip such as another shape of electrode.

The energy tip may be integrated into the waveguide. The entire assembly may move closer and further from the target as desired by the user. The energy tip may run the length through or alongside the entire length of the waveguide. The energy tip may also run through only a portion of the length of the waveguide and may come out a side of the waveguide.

The waveguide may be molded or extruded with various lumens or channels to collect smoke from the surgical field.

The device may include thermal management features such as including metal tubing or other heat conductive materials that are coupled to the waveguide or illumination element to act as heat sinks.

Optionally, the illumination element may be an LED, and the illumination element may be coaxial with the energy tip, or the waveguide may be coaxial with the energy tip.

Optionally, the waveguide may have microstructures on a surface thereof that shape the output light to have one or more desired optical properties. Optical coatings or claddings may be disposed on the inner or outer surfaces of the waveguide to provide desired optical properties. Air gaps may be formed or otherwise maintained adjacent the waveguide to minimize light loss.

In another aspect, a system for illuminating a surgical target comprises an illumination element, an optical waveguide, an electrode tip, and a heat sink. The optical waveguide transmits light emitted from the illumination element, and the electrode tip is adjacent the optical waveguide. The heat sink is thermally coupled with the illumination element and dissipates heat generated therefrom.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 16A-16D illustrate another exemplary embodiment of an illuminated energy tip.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

The present invention will be described in relation to illuminated energy hand-pieces used for example, during electrosurgery for cutting or coagulation of tissue. However, one of skill in the art will appreciate that this is not intended to be limiting and the devices and methods disclosed herein may be used with other instruments, and methods.

Figure 1A:
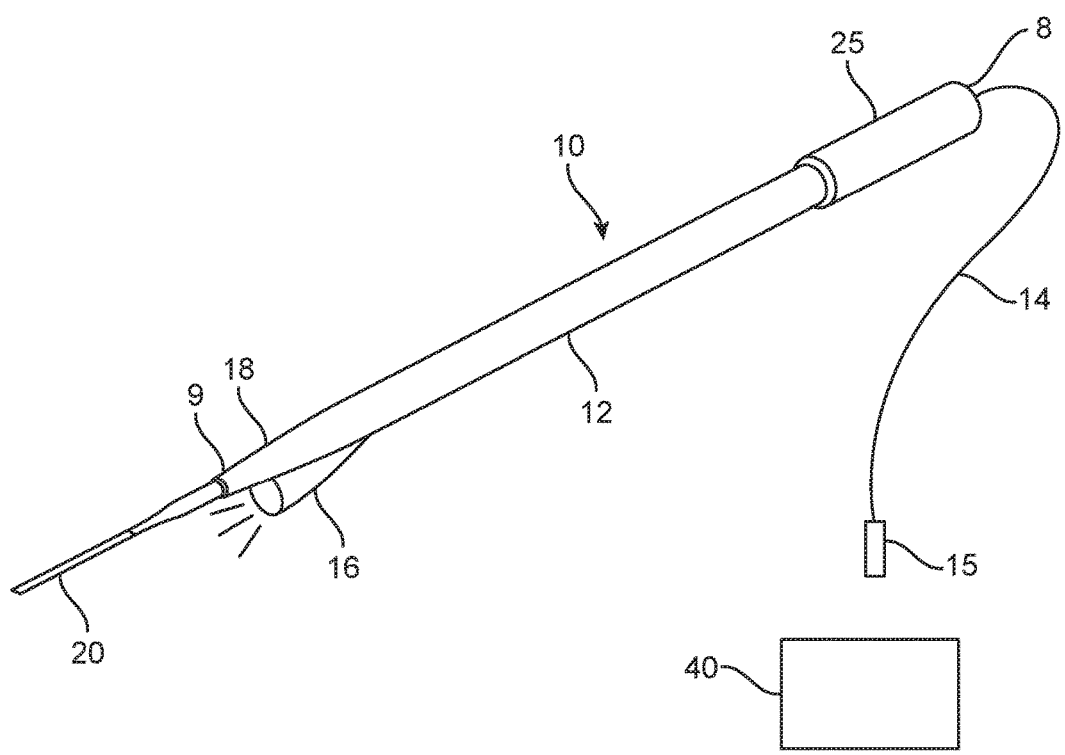
FIGS. 1A-1D illustrate standard illuminated energy hand-pieces.

FIG. 1A illustrates a standard illuminated energy hand-piece 10 which includes a handle 12, an energy tip or electrode 20, an unmounted illumination element 16, a cable 14 and an external power source 40. The external power source 40 may be used to provide energy such as RF energy to the electrode 20. Generally standard illumination energy devices have encapsulated power sources such as batteries in the handle or an external power source with a separate plug or connection. Because the illumination element is attached to a distal portion of the handle 12, light emitted from the illumination element 16 may not always have the desired intensity, directionality or uniformity or other desired optical properties when directed onto the surgical field. This may further be seen when different lengths of electrodes 20 are used with the handle 12 which would change the relative distance from the light source to the target, such as a surgical target. Since the intensity of light is inversely proportional to the square of the distance to the target, keeping the source as close to the target is desirable. Lenses may be used in conjunction with the illumination element 16, but these do not always provide the desired quality of light, especially since larger profile lenses are needed but these larger sizes are not always practical for a surgical application where space is very limited.

Figure 1B:
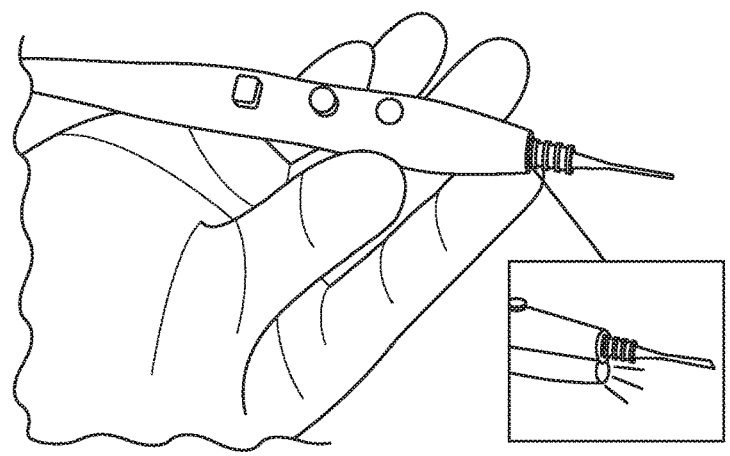
Figure 1C:
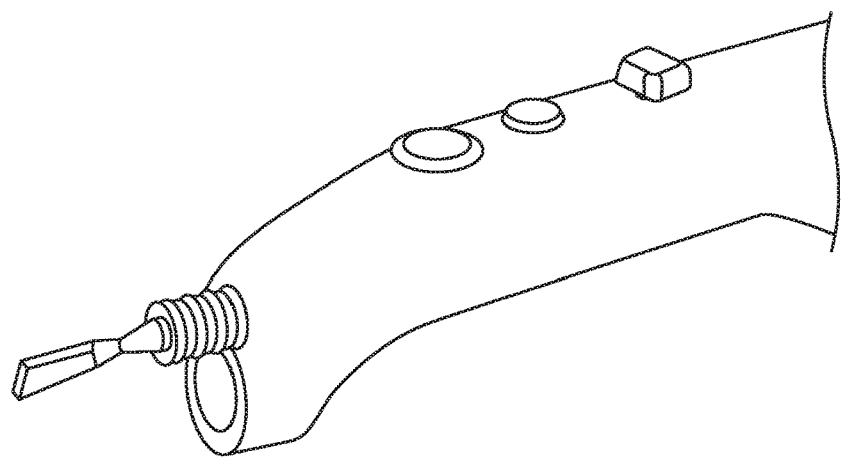
Figure 1D:
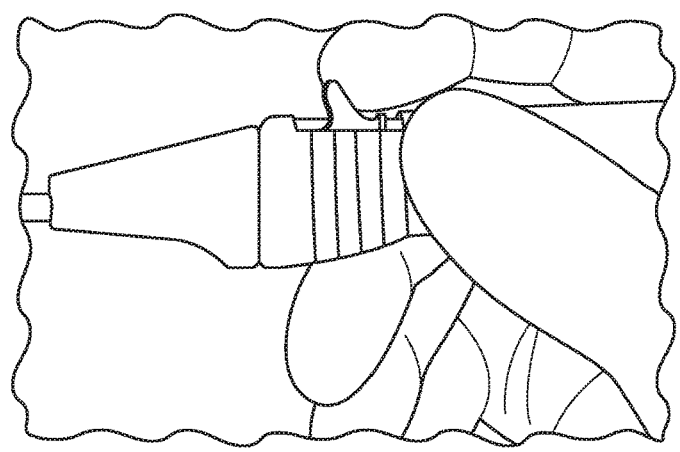

FIGS. 1B-1D illustrate exemplary illuminated electrosurgical instruments. FIG. 1B illustrates an electrosurgical pencil having an RF electrode and an LED illumination element. FIG. 1C highlights the tip of the device in FIG. 1B. Because the LED is attached to the pencil, if a long electrosurgical tip is used, the LED may be too far away from the surgical field to adequately illuminate the tissue in the surgical field. FIG. 1D illustrates another electrosurgical pencil having an illumination source disposed in the pencil of the instrument, thereby resulting in a large profile of the device which can obstruct access to the surgical field.

Some of the challenges mentioned above may be overcome with the exemplary embodiments of illuminated electrosurgical instrument described below.

Figure 2A:
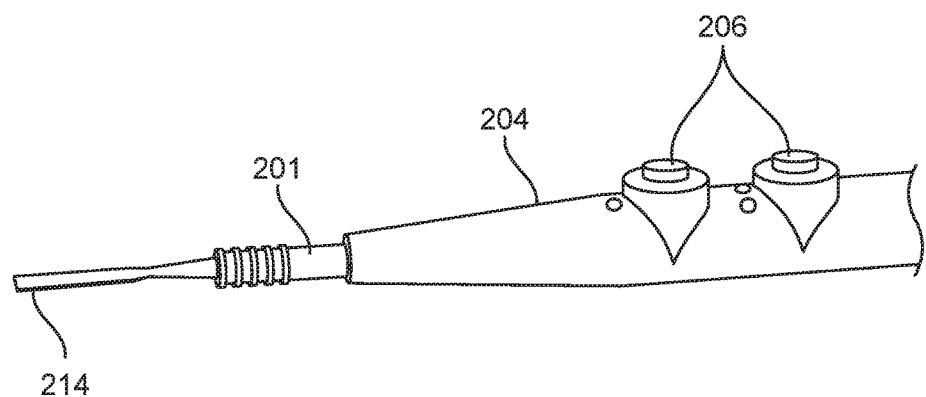
FIGS. 2A-2B illustrate an energy handpiece with an optical waveguide.

FIG. 2A illustrates an exemplary embodiment of an electrosurgical pencil. The distal tip includes an electrode 214 for delivering energy, typically RF energy to the tissue for coagulation or cutting. Control buttons 206 on the pencil 204 (also referred to as the handle) allow the surgeon or operator to control the mode of operation from cutting or coagulation. A plastic sheath 201 or sleeve having a textured surface, here several annular rings, provide a finger grip for the operator to easily grasp the electrode and remove it from the pencil 204.

Figure 2B:
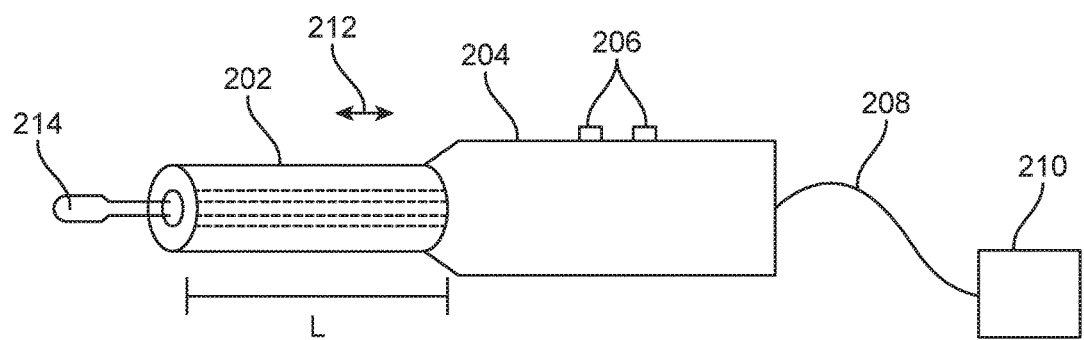

FIG. 2B illustrates an exemplary embodiment of an illuminated energy hand-piece having a handle 204 with an optical waveguide 202 coupled to a distal portion of the handle 204, and an electrode (also referred to as an energy tip) 214 extending distally from the waveguide 202. A cable 208 is coupled to the proximal portion of the handle and this operatively couples the energy hand-piece to an external power supply 210. The power supply 201 may provide RF energy to the electrode 214, and may also provide power to illumination elements (not shown) which deliver light to the waveguide 202. Optionally, the power source 201 may also include an external light source (e.g. a xenon lamp) which can deliver light via a fiber optic cable included in cable 208 to introduce light into waveguide. The optional light source may be integral with the power source or it may be a separate component. Control buttons 206 allow a user to turn the power on and off for delivery to the electrode 214. Often two buttons 206 are used, one for supplying RF current to the electrode that is optimal for cutting tissue, and the other button supplies RF current to the electrode that is optimized for coagulating. These controls may also automatically provide light to the waveguide which then illuminates the surgical field when current is delivered from the electrode to tissue. In some embodiments, a separate illumination control button may be disposed on the handle to active the light independently of the electrode power.

The electrode 214 may be fixedly attached to the waveguide 202 or the handle 204, or it may be detachably connected thereto which allows a user to replace electrode tips depending on the procedure being performed.

The optical waveguide 202 may be fixedly attached to the handle 204 or it may be adjustably attached thereto, such as with a movable connection 212 to allow the length L of the optical waveguide to be adjusted based on the length of the electrode. Any mechanism known in the art may be used to allow adjustment of the movable optical waveguide, such as a collet, a threaded connection, a pin and detent mechanism, a spring loaded mechanism, a ratchet and pawl mechanism, etc. LEDs in the handle or coupled to a distal portion of the handle, or coupled to the proximal end of the waveguide may supply light to the optical waveguide. Thus in this or any embodiment, the LED may move with the waveguide, and the waveguide may move independently of the electrode. Any number of configurations of this device are possible, as described below. The energy tip may therefore be fixedly connected to the waveguide and the tip may move together with the waveguide as it is slid or otherwise moved inward or outward, or the tip may be detachably connected to the waveguide and the tip may also move with the waveguide as it is moved inward or outward. In still other embodiments, the tip may be coupled to the handle, and the tip may remain stationary as the waveguide is moved, or the tip may be moved independently of the waveguide.

The optical waveguide in any embodiment may be a hollow tubular waveguide having a central channel extending through the tube, and with the electrode extending partially or all the way through the central channel or the optical waveguide may be a solid rod with no space between the electrode and conductor wire and the inner surface of the optical waveguide. In either embodiment, the optical waveguide may be fixed or adjustable. When the optical waveguide is fixed, it has a specific tube length that is attached to the handle.

In an alternative embodiment the sleeve may be integrated with micro LED dye, therefore the electrosurgical electrode tip can provide power to the sleeve to generate light. Thus, when the tip is inserted into the pencil and current is activated, current also flows to the LED.

Figure 3A:
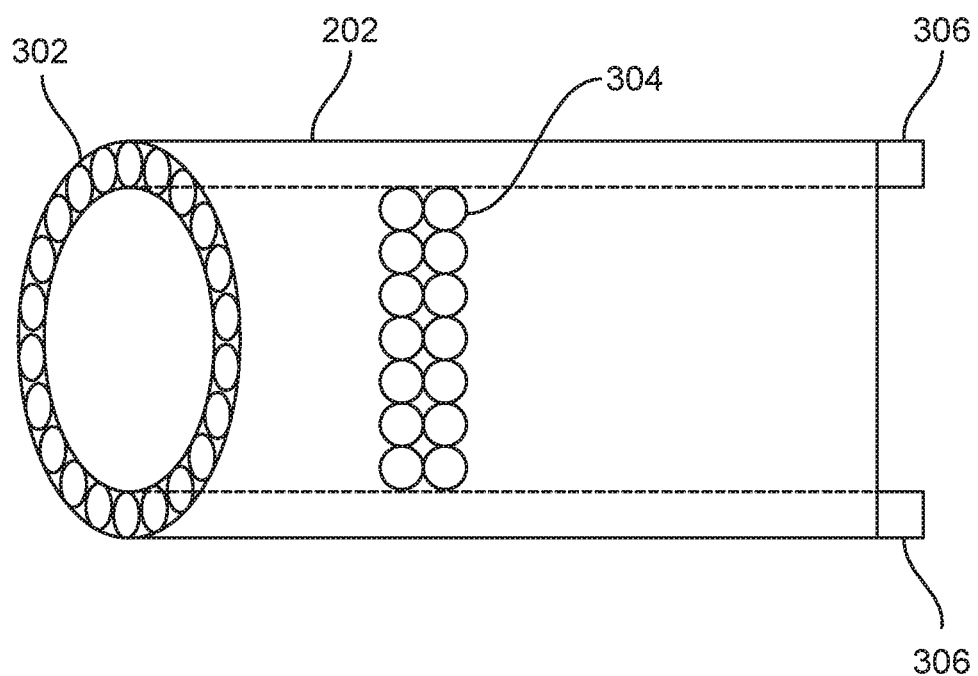
FIGS. 3A-3B illustrate an optical waveguide.
Figure 3B:
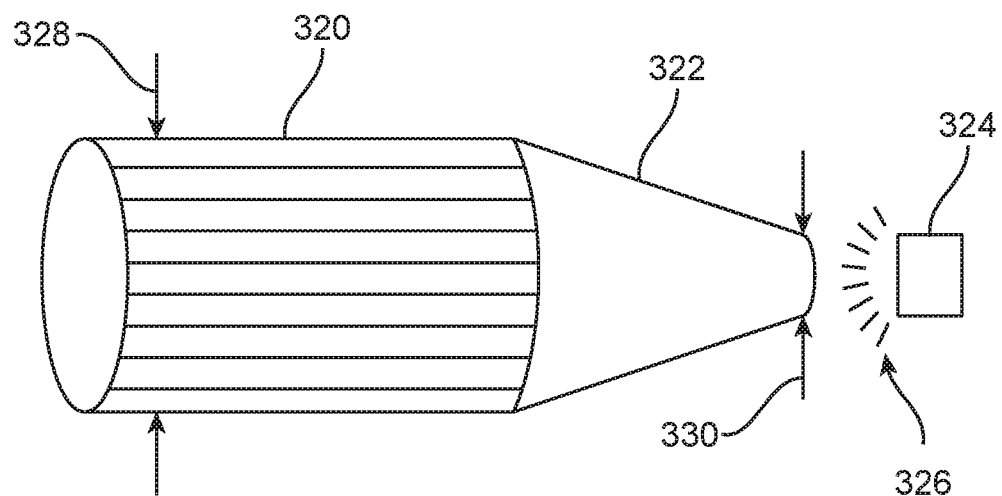

FIGS. 3A-3B show that any embodiment of the optical waveguide 202 may include optical structures such as lenslets 302 on the distal end of the tube, or the lenslets may be disposed on an inner surface, an outer surface, or any distal portion 304 of the tube. The lenslets help to extract and shape the light emitted from the waveguide. The proximal end of the waveguide may include LEDs 306 which provide light to the waveguide 202. The LEDs may be coupled to the waveguide in any number of ways, such as where the proximal end of the optical waveguide has a parabolic shape to capture the broad divergence of light emitted from a LED light source. In this embodiment, the ratio of the size of the waveguide diameter to the input size diameter of the parabola is preferably a minimum ratio of 2:1 as shown in FIG. 3B having LED light source 324 emitting light 326 into waveguide 320. The proximal portion of the waveguide has a parabolically shaped 322 input with an input diameter 330 as shown in FIG. 3B. The body of the waveguide is preferably cylindrically shaped and has a plurality of facets along the outer circumference to provide multiple surfaces against which the light may bounce, thereby allowing the light to mix better along the waveguide. The body of the waveguide has an output diameter 328 through which the light passes and then is extracted. In preferred embodiments, the ratio of the output diameter 328 to the input diameter 330 is at least 2:1. Alternative embodiments have LEDs positioned more distally located along the extended shaft, where the shaft may be composed of the waveguide, the LED section and a metal tube that provides heat sinking proximal to the LED source. The metal tube heat sink is described in more detail below. Additionally, the tube for heat sinking may be fabricated from any other material that dissipates heat.

Figure 4A:
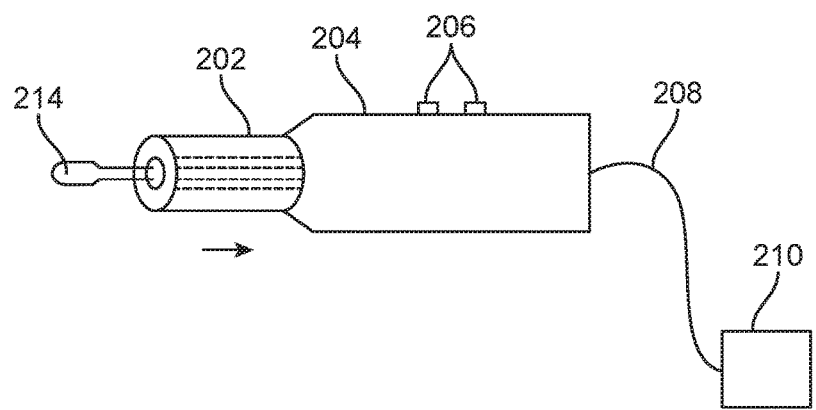
FIGS. 4A-4B illustrate a movable optical waveguide coupled to an energy handpiece.
Figure 4B:
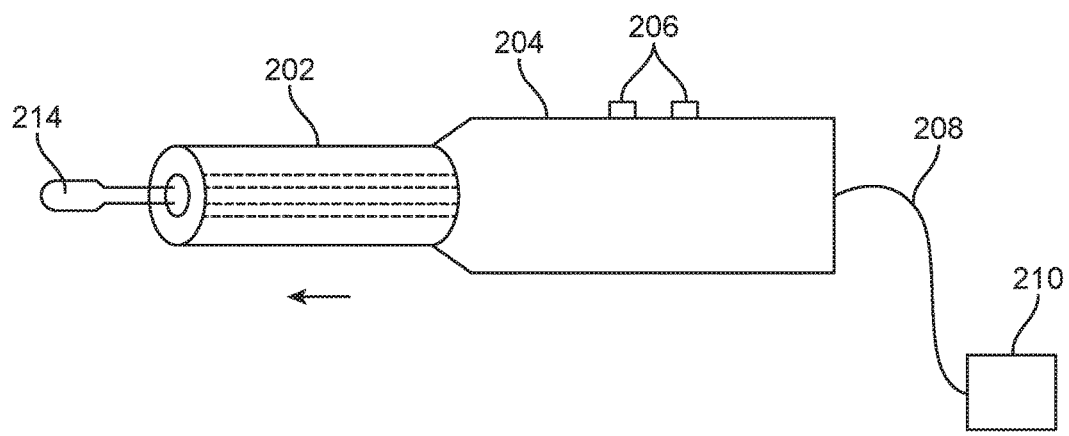

In some embodiments, the optical waveguide may slidably or otherwise extend away from or toward the handle. FIGS. 4A-4B illustrate this feature. In FIG. 4A the optical waveguide is collapsed into the handle, and in FIG. 4B the optical waveguide is extended outward away from the handle. The optical waveguide may be a fixed length, but may collapse into the handle so that the length of the exposed portion of the optical waveguide decreases, or the optical waveguide may extend away from the handle so that the length of the exposed portion of the optical waveguide increases. Various mechanisms for allowing the telescoping of the optical waveguide have been disclosed previously or are otherwise known in the art. Allowing the optical waveguide to be adjusted allows the user to bring the light closer to the work surface such as a surgical target, or the light may be moved away from the work surface. This may be advantageous when a surgeon uses various length energy tips with the handle so when a long tip is used, a longer optical waveguide is desired to ensure that the light is delivered close to the target tissue, and similarly, when a short tip is used, a shorter optical waveguide is preferred so that the tip of the waveguide is not too close to the work surface. Thus, a variable length optical waveguide allows a user to adjust length as required and to position the light output relative to the electrode tip.

Figure 15:
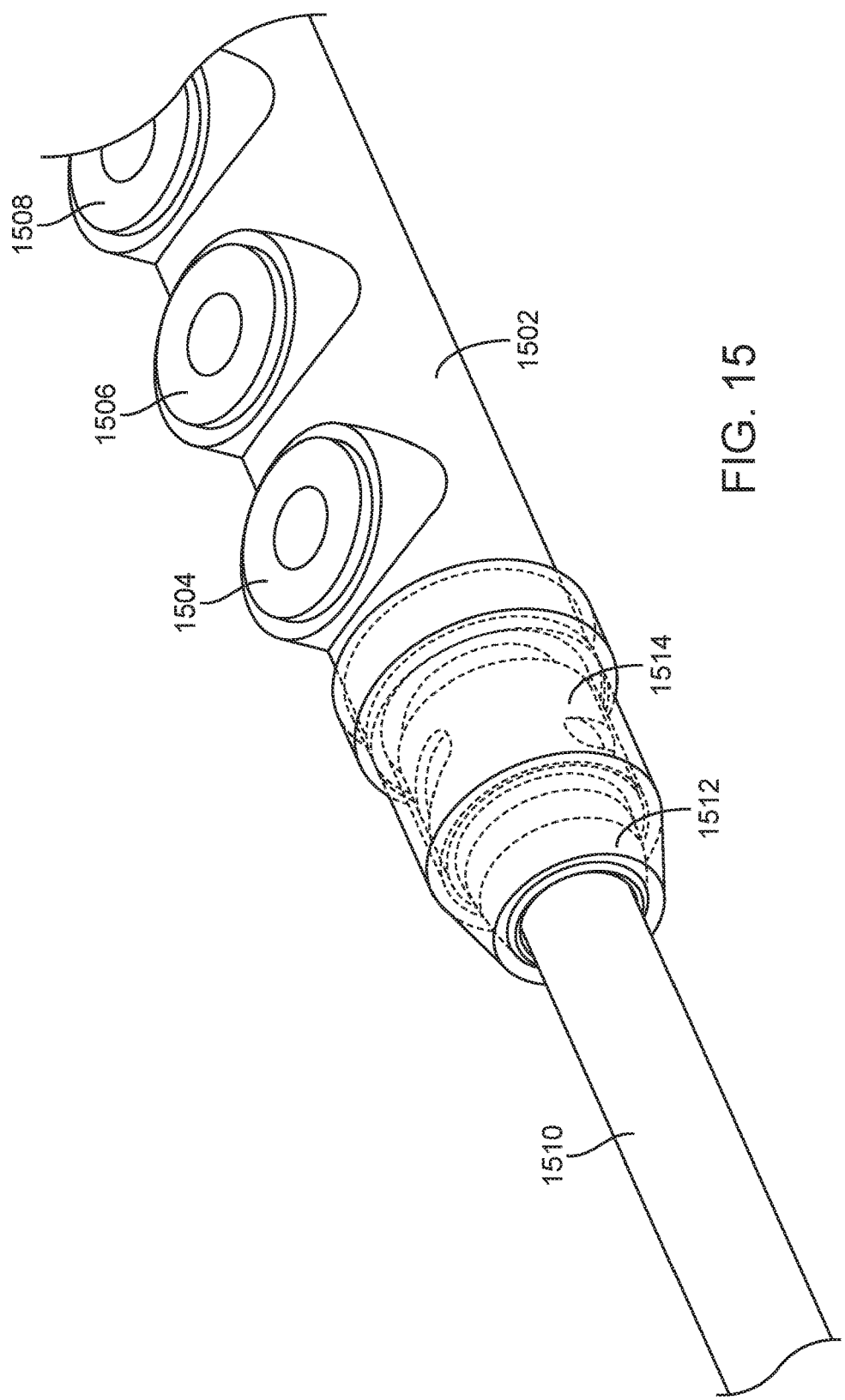
FIG. 15 illustrates an exemplary embodiment of a locking mechanism.

FIG. 15 illustrates an exemplary embodiment of a locking mechanism that may be used with any of the embodiments of movable waveguides or movable energy tips disclosed herein. A handle 1502 includes one or more control buttons, here three buttons 1504, 1506, 1508 which may be actuated by the user to turn the energy on or off in various modes. For example one button may be used to turn on and off RF cutting energy to the energy tip. The second button may be used to turn on or turn off coagulating RF energy to the energy tip. The third button may be used to turn on and off illumination from the energy tip without delivering energy to the energy tip. The third button may not be a button, and may instead be a switch such as a pressure sensor or other switch such as a foot switch, or slide. Depending on how the illumination element is coupled to the handle, the illumination element (e.g. a LED) may move relative to the buttons, or it may be fixed. A waveguide 1510 is disposed in the handle 1502 and it may extend outward or inward relative to the handle. The locking mechanism is preferably a "twist-lock" collet style mechanism that clamps circumferentially around an extendable shaft such as a waveguide or energy tip to securely hold it in place at any extended length and rotation. The locking mechanism consists of two pieces, a nose piece 1514 and a collet base piece 1512. When in the un-locked position the shaft or waveguide 1510 can freely rotate, extend, or retract through the inner diameter of the collet. When twisted a predetermined amount, here preferably 90 degrees, in a clockwise motion, the shaft is securely held in place and resists axial movement and rotation.

The collet base piece has a hollow inner diameter with a split tapered end and is designed for a round shaft to be fully inserted through the inner diameter. On the outer diameter of the base piece are two small protrusions (not seen in FIG. 15) that mate with two internal helix grooves on the inner diameter of the nose piece. These protrusions constrain the nose piece from coming free of the base piece and allow the nose piece to rotate a maximum of 90 degrees around the base. As the nose piece is rotated the helix grooves track along on the collet base protrusions and advance the nose piece in a downward direction. The nose piece and base piece have interfering tapers so as the nose piece is tightened against the base piece an inward radial force is created, thus making a secure clamping action around the extendable shaft. This locking mechanism may be used in any of the embodiments describe herein.

In any of the embodiments, the electrode tip may be disposed inside the hollow tube and as described above, the hollow tube may move independently of the electrode tip. Therefore an optical waveguide can slide relative to the length of the electrode tip which gives a surgeon flexibility to position the light at desired positions relative to the electrode tip. This also allows the surgeon to adjust the spot size of light emitted from the optical waveguide. Moving the optical waveguide distally moves the tip of the waveguide closer to the work surface therefore decreases the spot size, while retracting the optical waveguide proximally moves the tip of the waveguide away from the work surface, thereby increasing the spot size.

Any of the embodiments of optical waveguide may have a cylindrically shaped optical waveguide, or other shapes may also be employed such as square, rectangular, elliptical, ovoid, triangular, etc. In one example, flat facets can be used to provide better mixing of light in the waveguide. Odd number of facets is preferred. The number of facets is determined by the ratio of the sizes mentioned earlier. The more facets used, will push the outer waveguide shape closer to a circle, thus increasing the overall cross section size. Less facets will reduce the overall size of the waveguide. Some embodiments have a tapered optical waveguide such that the proximal portion of the optical waveguide has a larger size than the distal portion. In still other embodiments, the central channel of the hollow tube optical waveguide may be used to evacuate smoke from the surgical field. Thus, a vacuum is applied to a proximal portion of the optical waveguide to draw the smoke out of the surgical field and up into the central channel.

In other embodiments, the optical waveguide may be a solid rod such that there is no air space or gap between the electrode tip or conductor wire and the inner surface of the optical waveguide. As in previous embodiments, the solid optical waveguide may be fixedly coupled to the handle, or it may be adjustably attached to the handle so that its length may be adjusted to a desired position. The optical waveguide may have a central lumen through which a conducting element, such as a conductor wire or conductor rod is coupled to the electrode, or a proximal portion of the electrode tip may pass through the waveguide to occupy all of the space in the central lumen resulting in a solid waveguide. In some embodiments, this may be accomplished by over molding the waveguide onto the conducting element. The electrode tip may be coupled with the conducting element, or it may be integral with the conducting element. When the electrode tip is integral with the conductor element, the electrode tip is generally not exchangeable with other electrode tips. When the electrode tip is releasably coupled with the conductor element, it may be exchanged with other electrode tips. Preferred embodiments include a non-replaceable electrode tip which can be combined with the adjustable optical waveguide (e.g. slidable or otherwise moving waveguide) feature thereby allowing a user to adjust the light closer to, or away from the work surface for optimal lighting performance. Solid waveguides also provide additional benefits over hollow tube waveguides since they contain more material in the optical waveguide relative to a hollow tube waveguide which allows conduction of a greater amount of light. Additionally, a solid waveguide is structurally stronger than a hollow waveguide. Therefore, a stronger solid waveguide that can carry more light with a smaller profile is possible and preferred to a hollow tube which carries less light and may be weaker and have a larger profile relative to the solid waveguide. The conductor element passing through the solid waveguide also may provide strength to the waveguide.

Figure 5A:
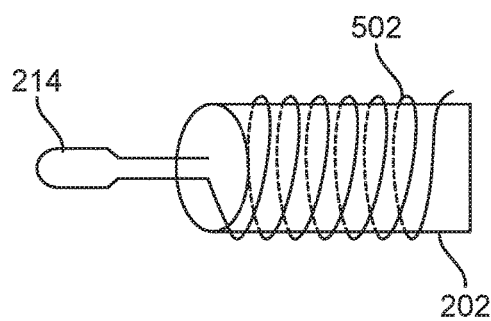
FIGS. 5A-5D illustrate exemplary embodiments of a conductor element adjacent the optical waveguide.
Figure 5B:
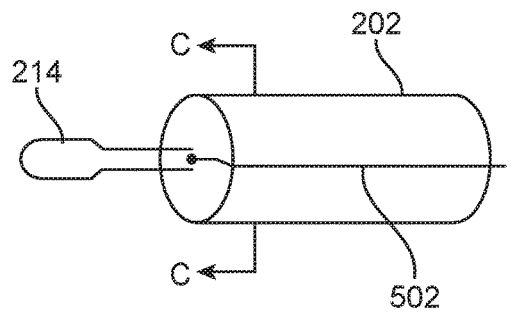
Figure 5C:
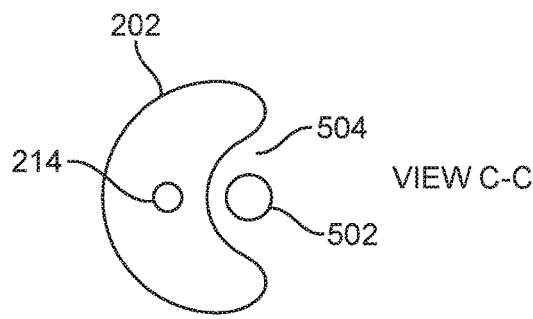
Figure 5D:
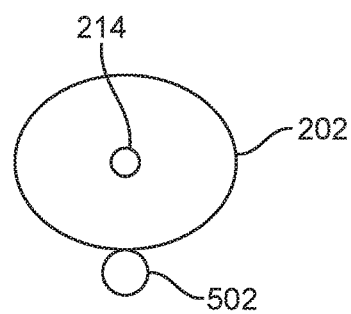

In some embodiments, the conductor element which passes through the waveguide, either a solid waveguide or a tubular waveguide, provides energy from a power source (e.g. RF power supply) to the electrode. In other embodiments, such as in FIG. 5A, the conductor element may be a wire 502 that is wrapped helically or otherwise around an outside surface of the optical waveguide 202 and coupled to the electrode tip 214. In FIG. 5B, the conductor element may be a wire 502 that runs along an outer surface of the waveguide. FIG. 5C shows an alternative embodiment of a cross-section taken along the line C-C in FIG. 5B where an optional concave cutout region 504 may be formed into the waveguide to accommodate the conductor element 502 to keep overall profile minimal. In a variation of the embodiment in FIG. 5C, the conductor element may be shaped to complement the concave region of the waveguide so that when the conductor element and the waveguide are fit together, they form a cylinder having a circular cross-section. In still other embodiments, a conducting metal tube (not illustrated) may be disposed around the waveguide similar to electrical cladding disposed over the waveguide. Here the energy tip is coupled to the outer conducting metal tube. FIG. 5D illustrates still another embodiment of a conductor element 502 coupled with an optical waveguide 202. In this embodiment the conductor element 502 is coupled to an outer surface of the waveguide and the conductor element runs axially therealong. The resulting cross-section forms a figure eight-like shape with a large profile waveguide and a smaller profile conductor element.

In any of the embodiments of the waveguide, a coating or cladding may be applied thereto in order to provide desired optical properties to the waveguide, thereby enhancing the efficiency of the waveguide. The coating or cladding may be applied to an outside surface of the waveguide, to the central channel of the waveguide, or to an outer surface of the conducting element in order to optically isolate the conductor element from the waveguide as well as to provide electrical or other insulation as required. The layer of cladding also provides a physical barrier to prevent damage to the waveguide from scratching, abrasion or other damage caused by adjacent surgical instruments. Optionally, any embodiment described herein may use air gaps disposed adjacent the waveguide to enhance optical transmission of light through the waveguide by minimizing light loss, as well as by using standoffs to maintain an air gap between the waveguide and adjacent components.

Figure 6A:
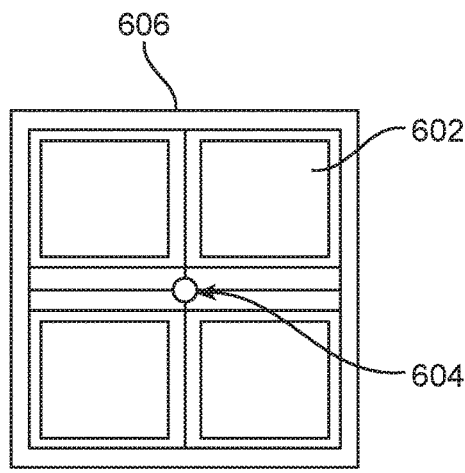
FIGS. 6A-6D illustrate an exemplary embodiment of an LED illuminated optical waveguide.
Figure 6B:
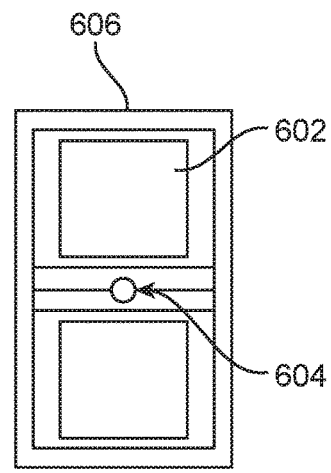
Figure 6C:
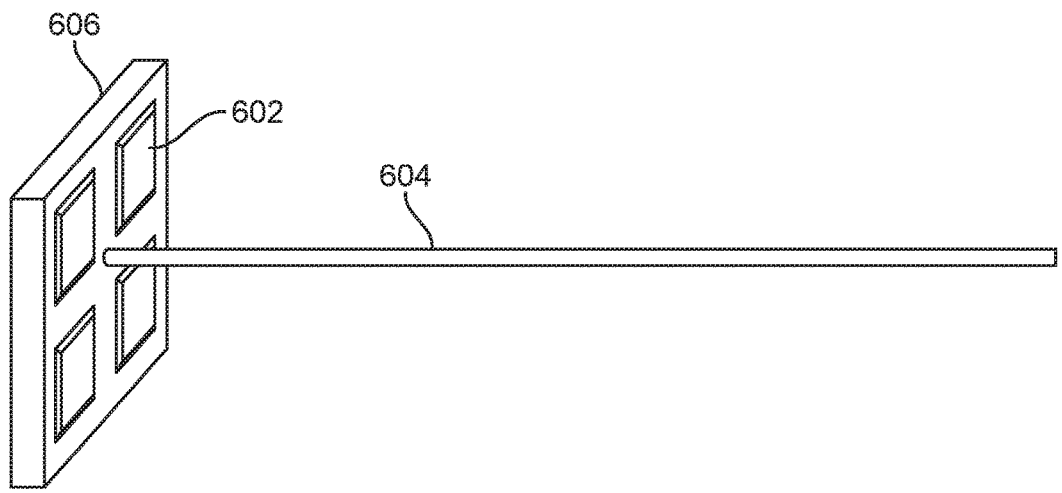
Figure 6D:
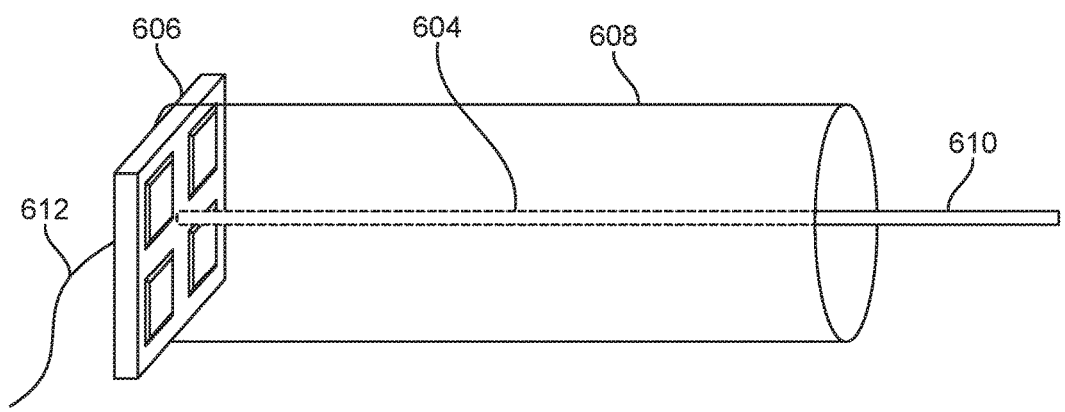

FIGS. 6A-6D illustrate an exemplary embodiment of an optical waveguide illuminated by LEDs. In FIG. 6A the LED board layout 606 includes an array of LEDs with dye elements 602 formed into a square pattern. Any number or combination of dye elements may be used in order to provide the desired light. A conductor element 604 passes through the center of the board layout 606. FIG. 6B illustrates an alternative board layout 606 having an array of two LEDs with dye elements 602 instead of the four LEDs illustrated in FIG. 6A. Any pattern and number of LEDs may be used. FIG. 6C illustrates the board layout 606 with the conductor element 604 passing through the board. FIG. 6D illustrates the board layout 606 coupled to the proximal portion of the optical waveguide 608 with a power cable 612 coupled to the board. The conductor element 604 extends axially through the waveguide with a distal portion 610 exposed so that it may be formed into an electrode tip or coupled with an electrode tip. Preferably the electrode tip is flat, and the conductor element may be round or flat in order to keep profile minimized. The optical waveguide 608 may be any of the embodiments of optical waveguides described in this specification. It may be a round cylinder or it may have a hexagonal, octagonal, or other polygonal shaped cross-section for facilitating mixing of the light passing through the waveguide as discussed previously. The polygonal shaped cross-sections preferably have flat planar facets around the outer circumference of the waveguide. The flat surfaces enable better mixing of light from the LEDs so that the image of the actual dye is not projected onto a target. The electrode tip is coupled directly to the LED board. The proximal end of the waveguide may be parabola shaped or have other custom shapes in or to provide better capture and mixing of light from the LEDs or other light source. This embodiment therefore preferably does not have a hole drilled through the waveguide to accommodate the conducting element. The conducting element fills the entire space in the waveguide and the two are integral with one another and the conducting element and the LED light source are integrated onto a single circuit board.

Figure 6E:
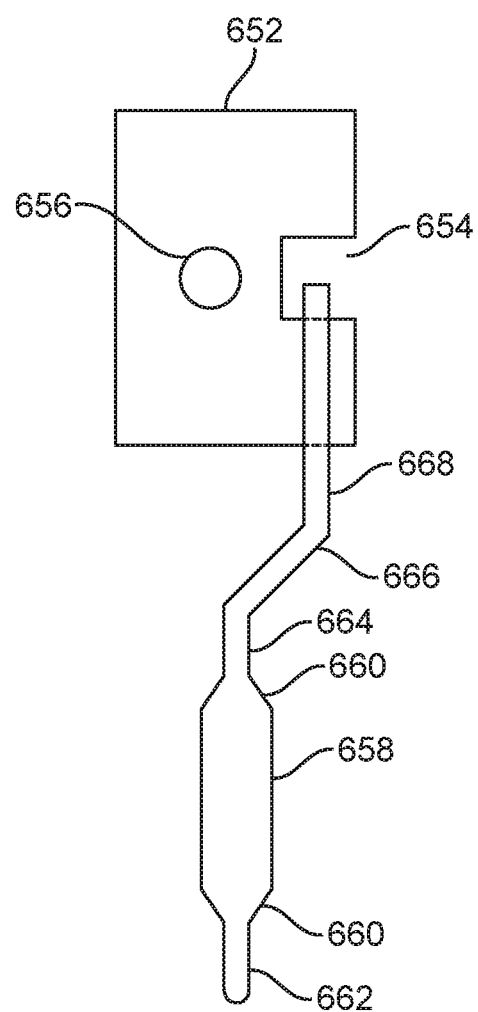
FIG. 6E illustrates another exemplary embodiment of an LED illuminated optical waveguide.

FIG. 6E illustrates an optional variation of the previous embodiment with the major difference being that only a single LED is used. The board 652 includes a recessed region 654 which is sized and shaped to receive a portion of the conductor 668 which is connected to the electrode tip 658. A single LED 656 is disposed on the board, and it is centered on the board so as to be coaxial with the central axis of the electrode 658, and also optionally with the waveguide. The electrode 658 may have any of the features of any of the electrodes described herein including coatings or other insulation layers, especially those described with reference to FIGS. 16A-16C. The electrode 658 includes a generally flat and planar section with proximal and distal tapered ends 660. The distal portion of the electrode forms an electrode tip 662 for delivering energy to tissue. The proximal portion forms an elongate arm 664 having an angled section 666 which couples the electrode to the conductor 668, thereby disposing the conductor off-center from the central axis of the electrode.

Figure 7:
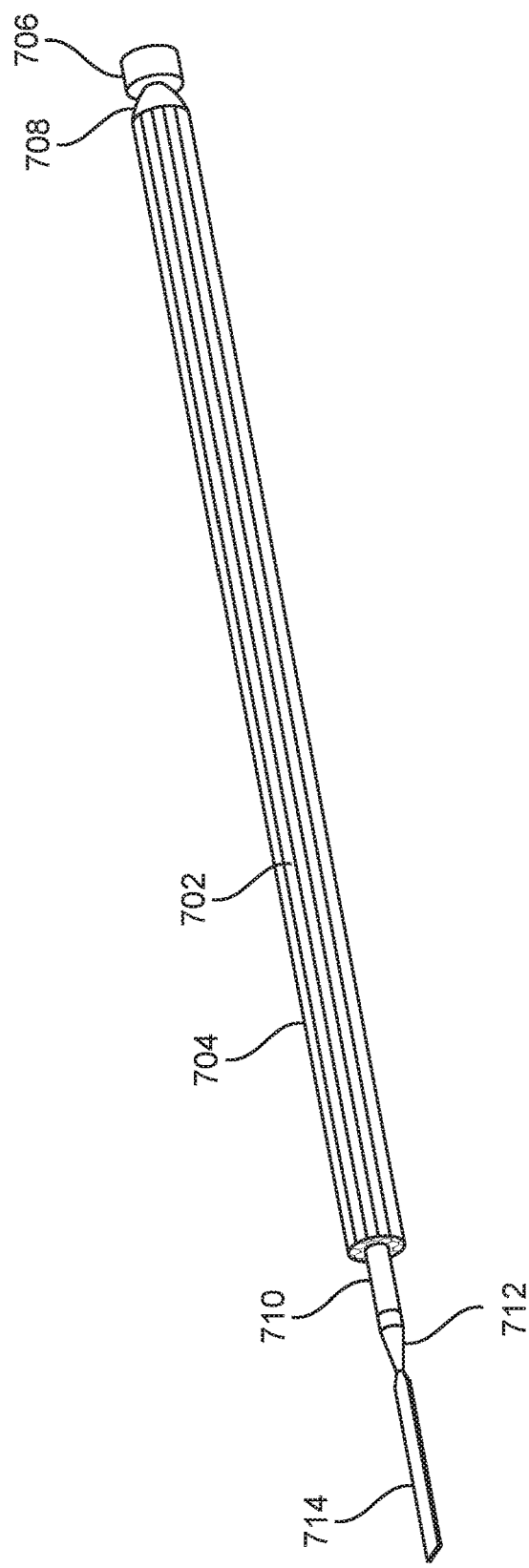
FIG. 7 illustrates an exemplary embodiment of an optical waveguide with electrode.

FIG. 7 illustrates an exemplary embodiment of an optical waveguide 702 with electrode tip 714. The electrode tip 714 is a flat planar shape and is coupled to a conductor element 712 which extends through the waveguide 702. A layer of cladding 710 is disposed over the conductor element in order to isolate it from the waveguide 702. Additionally, a layer of cladding 704 is disposed over the outer surface of the waveguide 702 to isolate it from blood or contaminants. The waveguide in this embodiment is a polygonal shape (e.g. hexagonal, octagonal, etc.) having flat planar facets on the outer surface. A LED 706 is coupled to the proximal end of the waveguide, and the proximal end of the waveguide is parabolically shaped 708 in order to receive a maximum amount of light from the LED. Other coupling means can be used to optically couple the LED to the waveguide, such as by using lenses, hollow reflectors, gradient lenses, etc. Also, coatings may be applied to the waveguide to enhance coupling efficiency. The illumination element 706 may be an LED or LED array, including any of the LED embodiments disclosed herein.

Figure 8:
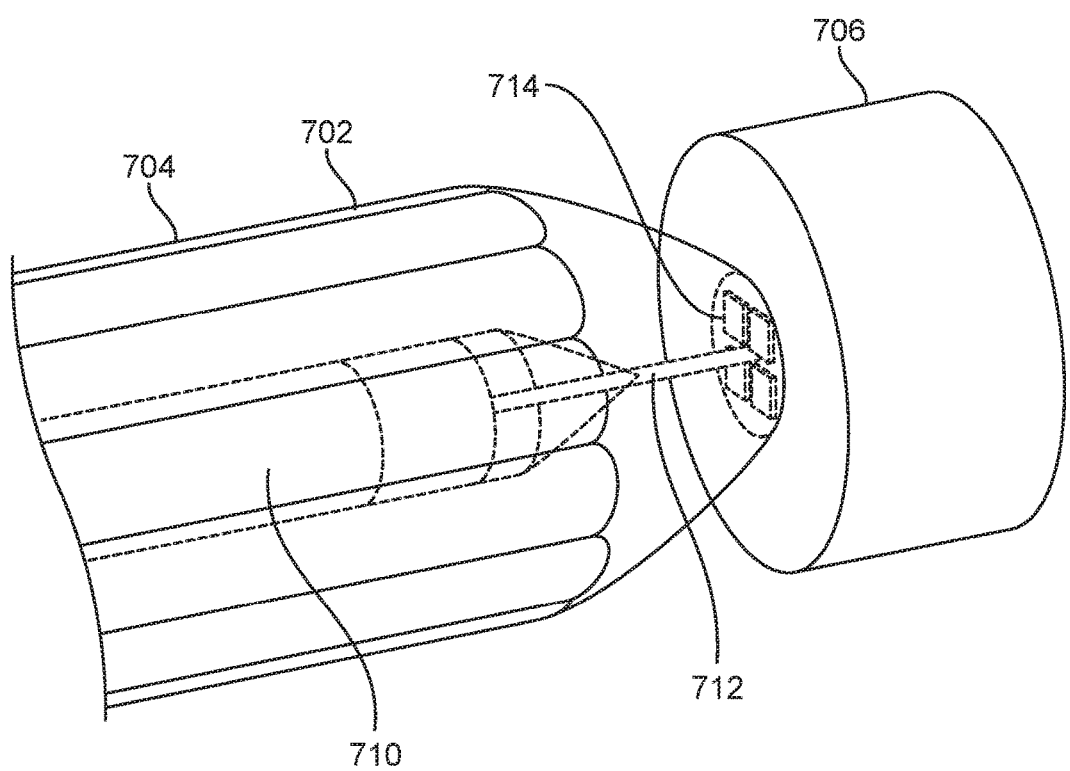
FIG. 8 highlights the proximal portion of the waveguide in FIG. 7.

FIG. 8 illustrates the proximal portion of the waveguide 702 in FIG. 7. The conductor element 712 extends all the way through the waveguide and exits the proximal-most end of the waveguide and is coupled with the illumination element 706. The conductor element may be electrically bonded to the illumination element 706 or it may be disposed in a hole that extends through the illumination element 706. The illumination element in this embodiment is an array of LED elements 714 which generally takes the same form as described in FIGS. 6A-6D. Additionally, the proximal portion of the waveguide is parabolically shaped in order to capture a maximum amount of light from the LEDs. Cladding 710 is seen disposed over the conductor element 712 to isolate the conductor element from the waveguide and this helps prevent light loss from contact between the two components. Also, as disclosed previously, air gaps may be used to help minimize light loss.

Figure 9:
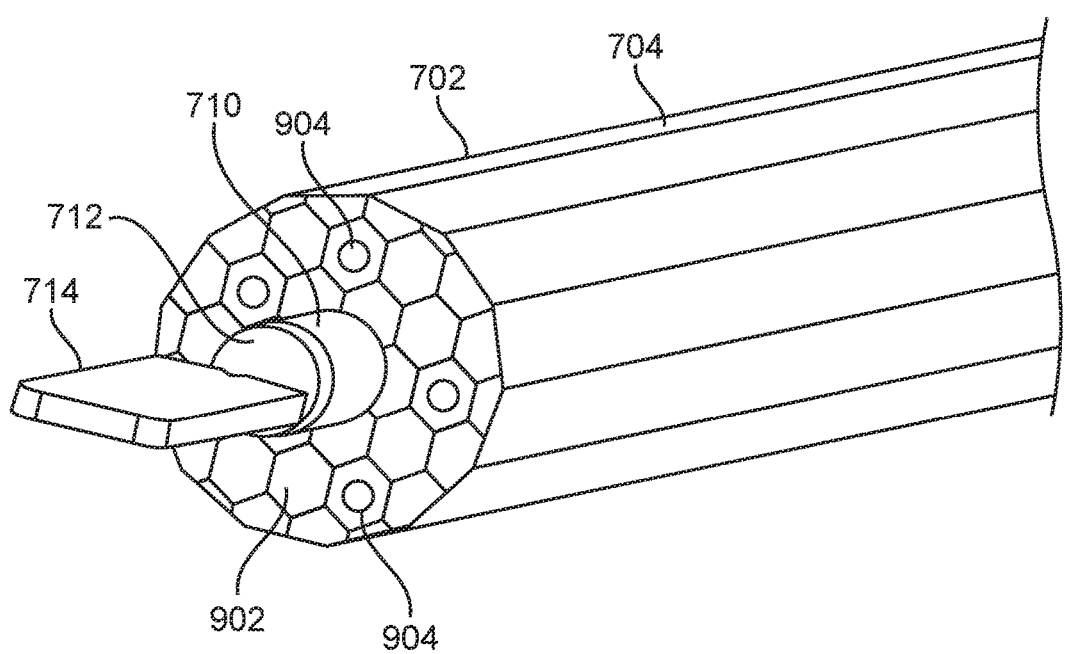
FIG. 9 illustrates an exemplary embodiment of an illuminated electrode tip with smoke evacuation.

Any of the embodiments of illuminated electrode tips may also include a smoke evacuation feature. FIG. 9 illustrates an exemplary embodiment of an illuminated electrode tip with smoke evacuation lumens (also referred to as channels). The optical waveguide 702 includes cladding 704 disposed over the outer surface of the waveguide. The conductor element 712 extends through the waveguide and a layer of cladding 710 is disposed over the conductor element. Electrode tip 714 is coupled with conductor element 712. The electrode may be bent relative to the conductor element or the optical waveguide. Optional lenslets 902 are provided on the distal face of the optical waveguide in order to shape the light exiting the waveguide to provide a desired illumination pattern on the target, here a surgical target. Smoke evacuation channels 904 may extend axially all the way through the waveguide to the proximal end thereof where the evacuation channels are coupled to a vacuum so that suction may be applied to the channels to draw out smoke created during electrosurgery. In other embodiments where the optical waveguide is a hollow tube, the central channel of the hollow tube may be used for smoke evacuation.

Figure 10:
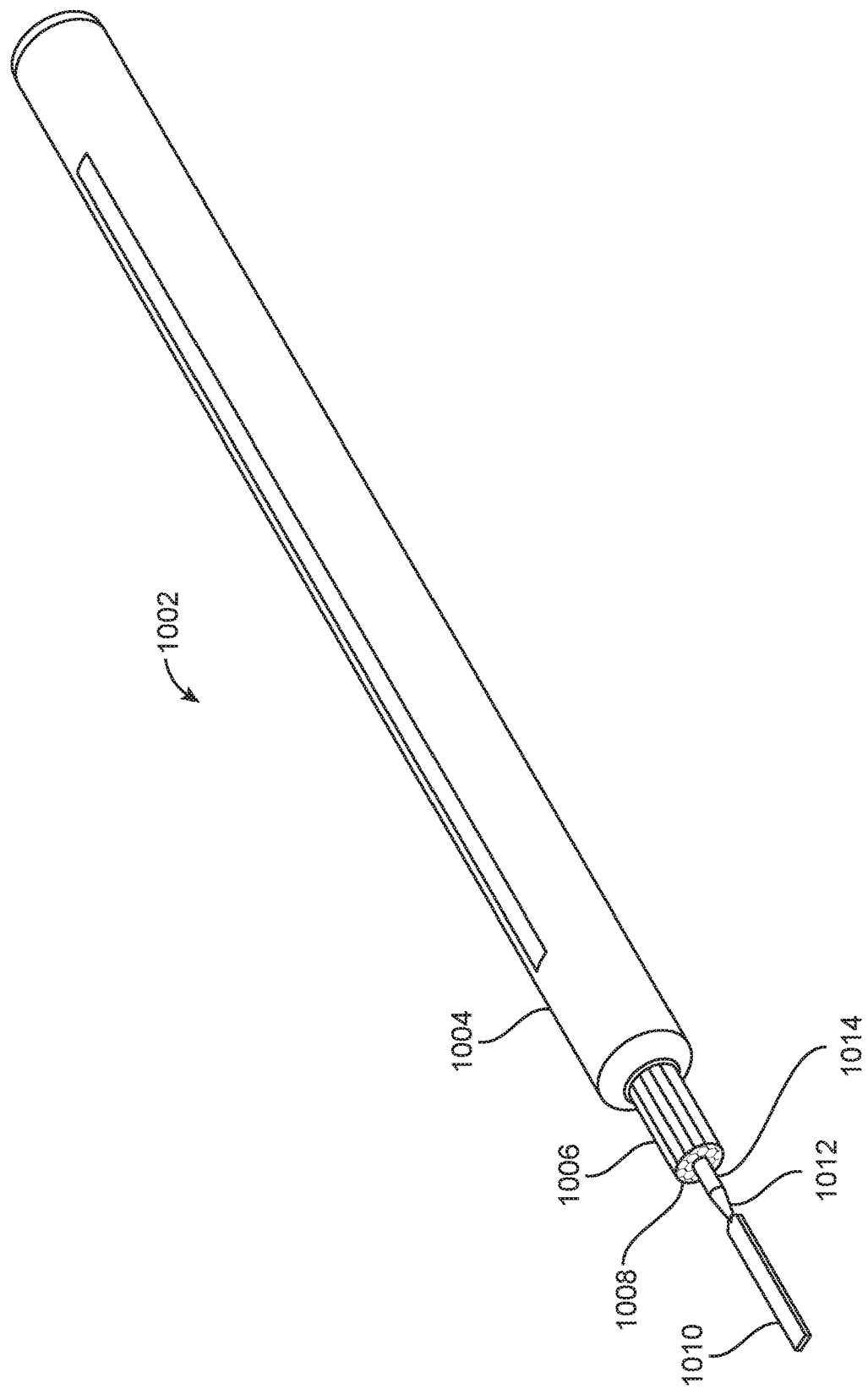
FIG. 10 illustrates an exemplary embodiment of an illuminated hand-piece with energy tip.

FIG. 10 illustrates another exemplary embodiment of an illuminated energy tip and hand-piece 1002 which demonstrates many of the individual features previously described above combined into one embodiment. The illuminated energy tip and hand-piece 1002 includes a handle 1004, an optical waveguide 1006, conductor element 1012 and energy tip 1010. The optical waveguide 1006 is preferably coaxially disposed in the handle 1004 and coaxial to the tip 1010 and may be either fixed to the handle or slidably adjustable as described above so that the exposed length of the waveguide 1006 may be increased or decreased as required. The waveguide 1006 preferably has a plurality of flat planar facets which form the polygonal outer surface of the waveguide, and this shape as discussed previously helps light mixing in the waveguide. Optional tube 1015 is disposed over the waveguide and is made from a heat conductive material and acts as a heat sink to conduct heat away from the device. Additionally, optional lenslets 1008 are disposed on the distal end of the optical waveguide to shape and direct the light so that the beam of light illuminates the surgical target properly. An optical cladding such as a polymer like fluorinated ethylene propylene (FEP), or a heat shrink may be disposed over the waveguide to isolate it from direct contact with the handle, thereby minimizing light leakage and protecting it from damage caused by contact with adjacent surgical instruments. A conductor element 1012 extends preferably coaxially through the optical waveguide and into the handle 1004 and provides energy to the tip 1010. The energy tip 1010, here a flat planar blade is coupled to the conductor element. A thin neck region may be used to couple the energy tip with the conductor element so that the energy tip may be bent into a desired shape during use. An optical cladding and/or insulation layer 1014 may be disposed over the conductor element to isolate it from the optical waveguide. The layer of cladding or insulation 1014 helps to prevent light leakage from the optical waveguide and also may help prevent energy from leaking from the conductor element.

Figure 11:
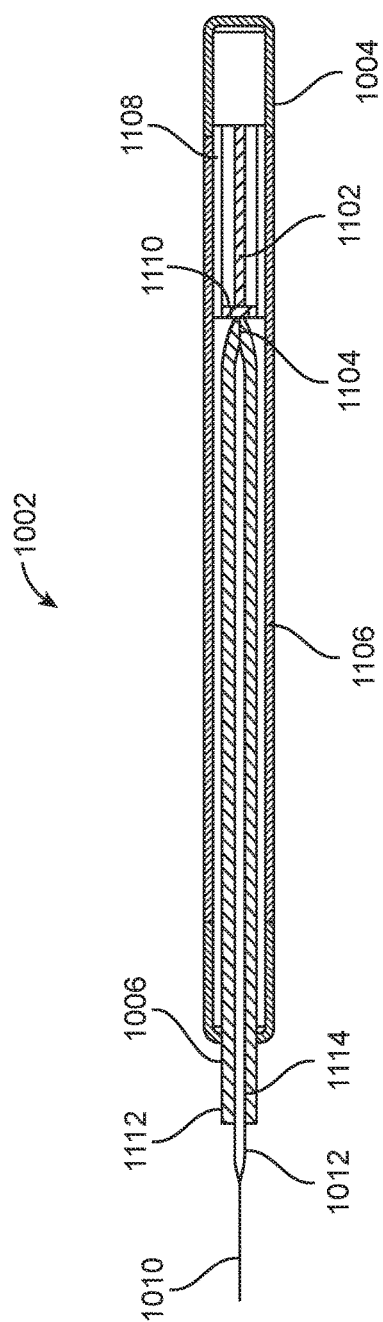
FIGS. 11-12 illustrate cross-sections of exemplary embodiments of illuminated hand-pieces with an energy tip.

FIG. 11 illustrates a cross-section of the device 1002 in FIG. 10 and highlights the relationship of some of the elements of the device. For example, energy tip 1010 is coupled with conductor element 1012 which extends through the waveguide 1006. An outer FEP (fluorinated ethylene propylene) cladding 1112 is disposed over the waveguide 1006 and an inner layer of FEP cladding 1114 is disposed over the conductor element 1012. The waveguide and conductor element extend preferably coaxially through the handle 1004. An outer heat sink 1106 maybe coupled to an inside surface of the handle to help dissipate heat from the waveguide. This heat sink may be a metal cylinder extending axially along the longitudinal axis of the handle or it may be made from other heat conductive materials than can act as a heat sink. A small wire channel 1104 may extend through the proximal end of the waveguide in order to allow the conductor element or a wire coupled to the conductor element to pass through the proximal end of the waveguide which in this embodiment is preferably a parabolically shaped proximal end similar to those previously described. A metal core LED printed circuit board (PCB) 1110 and this may have the LEDs as described elsewhere in this specification. An inner heat sink such as a metal tube 1108 may be butt coupled or otherwise coupled to the proximal end of the waveguide to further help dissipate heat from the waveguide, and an elongate portion 1102 of the PCB may extend axially away from the LED PCB to the proximal end of the handle where it may be coupled with a fitting or connector to allow it to be operatively coupled with an external power source, or other service. In this embodiment, the waveguide has a length that is longer than the length of the inner heat sink. In alternative embodiments, instead of, or in addition to the inner heat sink butt coupled with a proximal end of the waveguide, a heat sink tube maybe disposed over the waveguide to partially or fully enclose the waveguide and dissipate heat. The assembly may therefore have a metal tube heat sink, the waveguide and any of the LED embodiments, along with any of the energy tips and handle embodiments.

Figure 12:
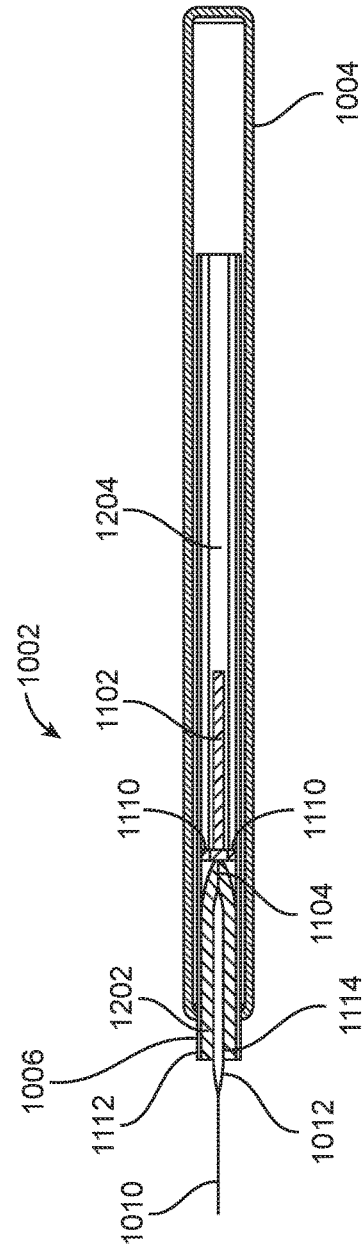

FIG. 12 illustrates an exemplary embodiment of an illuminated hand-piece with an energy tip that is substantially the same as the embodiment in FIG. 11 with the major difference being that the waveguide 1202 is considerably shorter than the inner heat sink 1204. The inner heat sink 1204 is coupled to the proximal end of the waveguide 1202. In any of the embodiments, the inner heat sink tube 1204, 1108 may also be conductive to provide energy to the LED PCB or the energy tip.

Figure 13A:
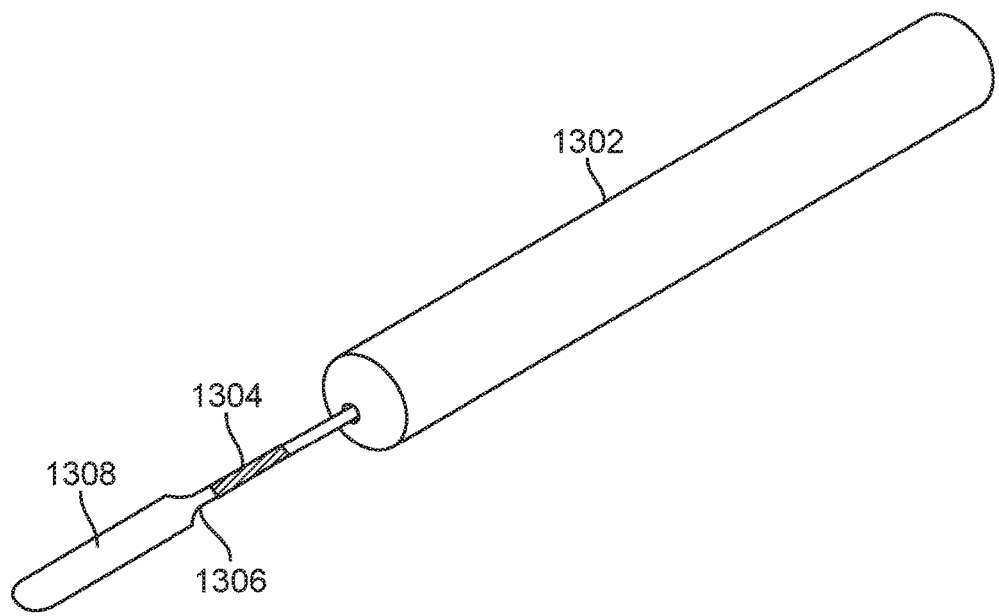
FIGS. 13A-13B illustrate exemplary embodiments of an illumination element coupled to an energy tip or conductor element.
Figure 13B:
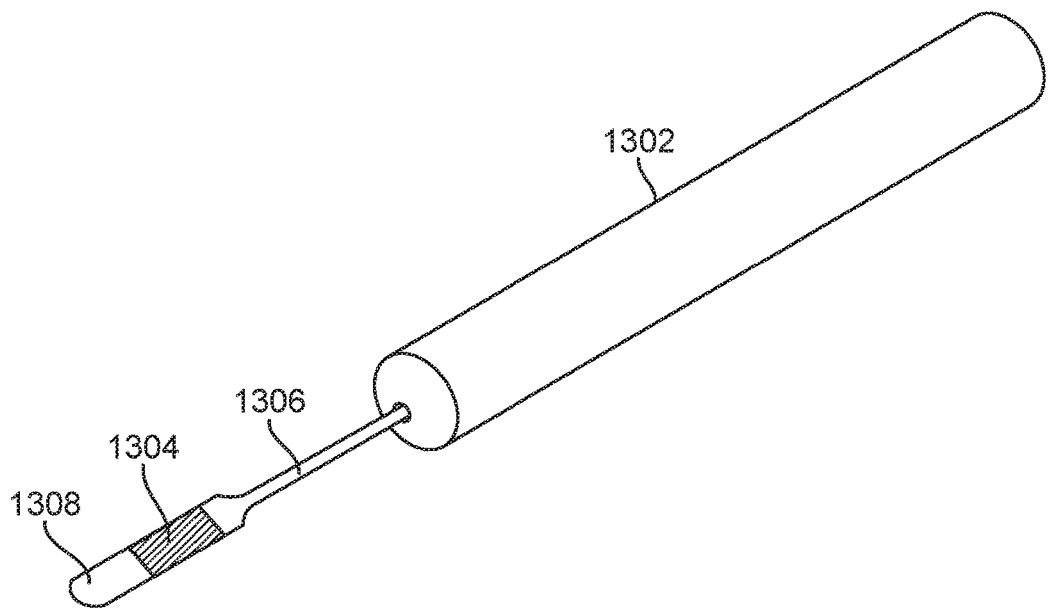

FIGS. 13A-13B illustrate exemplary embodiments of an illumination element coupled to an energy tip or conductor element. The illumination element is preferably a waveguide such as those described herein, but may be any illumination element including those disclosed herein. The energy tip similarly may be any energy tip disclosed herein. The energy tip 1308 is coupled to a conductor element 1306 which is coupled to a handle 1302. The waveguide may be a rigid or malleable waveguide 1304 which is coupled to the conductor 1306 in FIG. 13A, while in FIG. 13B the waveguide 1304 may be rigid or malleable and is coupled to the energy tip 1308. This provides lighting that is close to the energy tip. In any embodiment, the energy tip may be fixedly coupled to the conductor element or to the handle, or the energy tip may be releasably coupled to the conductor element or the handle. The energy tip, conductor element, waveguide, or handle may be any of the embodiments disclosed herein. The waveguide may be formed from any of the waveguide materials disclosed herein.

Figure 13C:
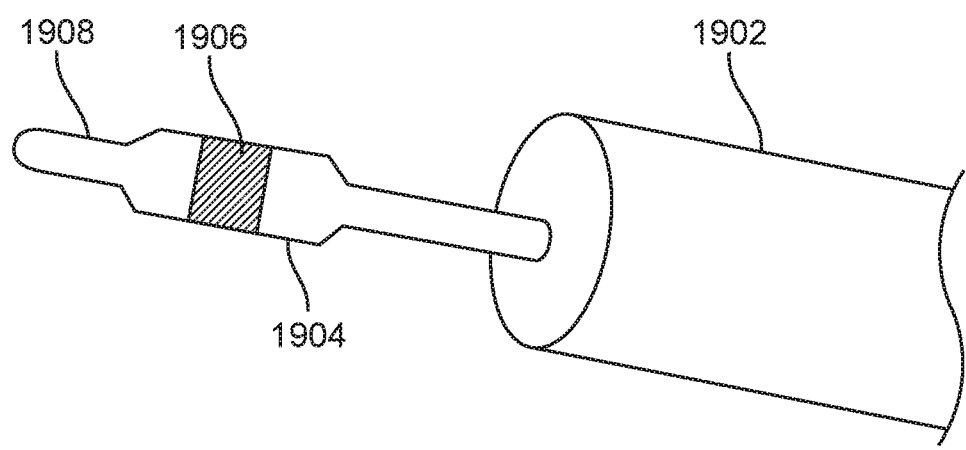
FIG. 13C illustrates a coating on the electrode.

FIG. 13C shows the use of an optional coating on the electrode of FIGS. 13A-13B or any of the electrodes described herein. The electrode 1904 is at least partially disposed in the waveguide 1902 which is then movably coupled to an electrosurgical pencil or other handle. A portion of the electrode 1906 may be coated with glass and/or may be polished in order to help reflect light emitted from the waveguide 1902. The light is preferably reflected toward the tip and toward target work area and this can help minimize glare emitted toward a surgeon or other operator. The coated portion 1906 may be selectively disposed on only a portion of the electrode, or it may be disposed on the entire portion of the electrode. The coating may also be on a distal portion 1908 adjacent the portions of the electrode where energy is delivered to target tissue.

In any of the embodiments, the LED may be disposed in a number of positions other than just at the proximal end of the waveguide. For example, the LED may be positioned between the proximal end and the distal end of the waveguide, or the LED may be positioned at the distal end. Additionally, the LED may be positioned in any number of orientations relative to the waveguide.

Figure 14A:
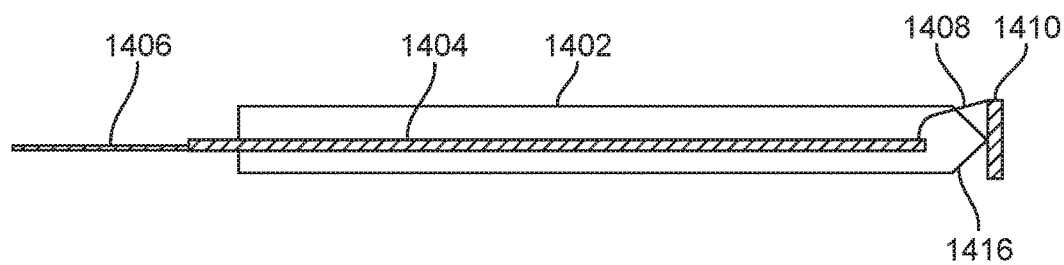
FIGS. 14A-14C illustrate alternative positions of an illumination element relative to a waveguide.
Figure 14B:
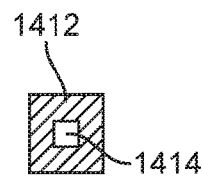
Figure 14C:
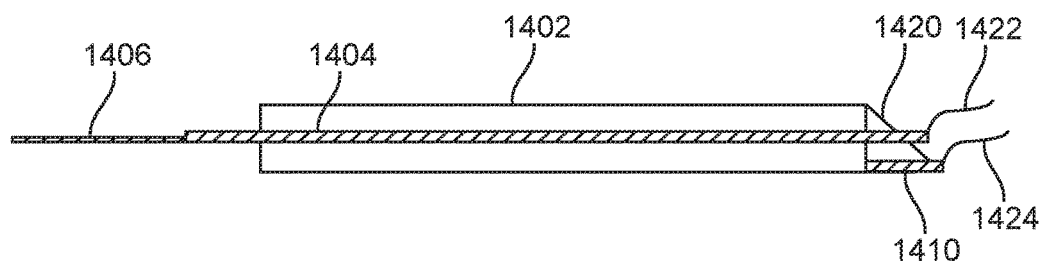

FIGS. 14A-14C illustrate alternative embodiments with varying LED positions. FIG. 14A illustrates an energy tip 1406 coupled to a conductor element 1404 which extends through waveguide 1402. A conductor element such as a wire 1408 is coupled to electrical connection 1412 (as best illustrated in FIG. 14B) on the LED board 1410 and supplies energy to energy tip 1406 such as RF energy. A single LED 1414 or an array of LEDs may be disposed on the LED board 1410. In this embodiment, the LED board is disposed against a proximal portion of the handle and waveguide 1402. A parabolic shaped 1416 proximal portion of the waveguide receives light from the LED. FIG. 14B illustrates an end view of the LED board. The LED board is preferably transverse to the longitudinal axis of the waveguide. A single LED may be coaxial with the electrode tip and the board may lie in a plane that is generally orthogonal or otherwise transverse to the axis of the waveguide. The board may help dissipate heat into the heat sink that may be surround the waveguide or that is butt coupled to the board. Optionally, in any embodiment the waveguide may be coaxial with the electrode.

FIG. 14C illustrates an alternative embodiment where the LED board 1410 is oriented generally parallel to the longitudinal axis of the waveguide 1402 and is disposed adjacent a proximal end of the waveguide. An angled parabolic section 1420 of the waveguide receives the light from the LED and transmits it distally toward the energy tip 1406. In this embodiment, a conductor element such as a wire 1422 is coupled to the conductor element 1404 for providing energy to the energy tip 1406. Also, a conductor element 1424 provides power to the LED board. Other positions for the LED along the waveguide are contemplated and these embodiments are not intended to be limiting.

FIG. 16A shows an exploded view of another exemplary embodiment of an illuminated energy tip 1602 which may be coupled to a handpiece such as an electrosurgical pencil (not illustrated). One advantage of this embodiment is that the light and the electrode may be rotated together, thereby ensuring uniform lighting of the target tissue. The illuminated energy tip 1602 includes an anodized aluminum shaft 1600, FEP cladding 1604, an LED board 1606, waveguide halves 1608, and an electrode blade 1612. The waveguide may be molded as a single unit as described elsewhere in this specification, and therefore does not necessarily have two halves coupled together.

Figure 19A:
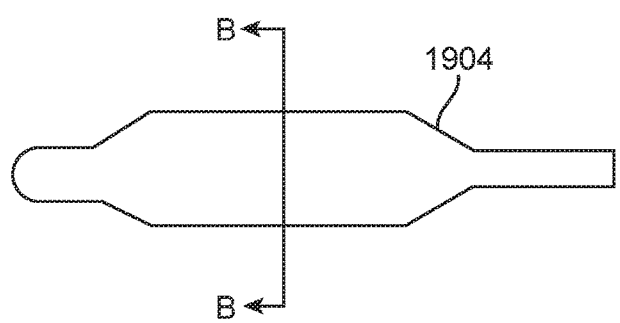
FIGS. 19A-19D show various electrode cross-sections.
Figure 19B:
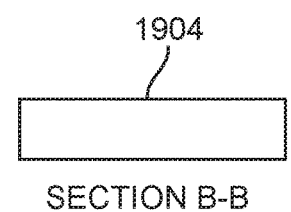
Figure 19C:
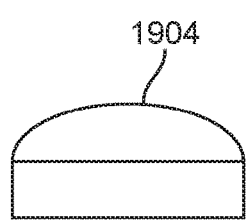
Figure 19D:
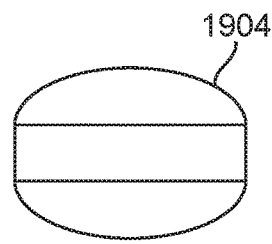

The electrode blade 1612 preferably includes a distal portion which is used to deliver energy (preferably RF energy) to tissue in order to cut or coagulate the tissue. This distal section 1616 is preferably insulated with a layer of material, here preferably a glass coating. The glass coating is advantageous since it has desirable optical properties and is distal to the waveguide 1608 and therefore helps to ensure that light emitted therefrom is properly reflected from the waveguide toward the surgical target area and minimizes glare back toward the surgeon or other operator. The tip is preferably insulated by a Teflon (polytetrafluorinated ethylene, PTFE) coating. This coating will scatter and absorb light. Having a reflective surface on the tip will aid the efficiency of the device by reflecting the light from the waveguide off the surface of the tip towards the target and therefore reduce unnecessary scatting. The tip can also have various shapes to aid in dispersion of light. The tip may have a curvature or taper. For example, FIG. 19A illustrates a top view of an electrode 1904. FIG. 19B shows a cross-section of the electrode 1904 taken along the line B-B and shows upper and lower flat planar surfaces while FIGS. 19C and 19D show optional convex upper and lower surfaces. The dikal portion may be thin enough to allow an operator to bend the tip in order to conform to the anatomy being treated. A middle section 1614 of the electrode blade 1612 is preferably also insulated, here preferably with FEP (fluorinated ethylene propylene) in order to prevent energy from leaking out of the electrode along the middle section, and also the FEP provides an index of refraction lower than the index of refraction of the waveguide 1608 thereby helping to prevent or minimize light leakage from the waveguide due to contact between the waveguide and electrode blade. A low index of refraction coating or air gaps may also be used in conjunction with or instead of FEP to provide similar results. A proximal portion of the electrode includes a thin elongate section which serves as a conductor element and allows the electrode to be coupled to wires in the handle (not shown) which are operably connected to the power supply, preferably an RF generator. The proximal portion of the electrode may be straight and linear, or it may have an angled section so that a proximal portion of the thin elongate section is off-center, allowing it to pass through the LED board 1606 off center. Optionally, the proximal portion of the electrode may also be straight and pass through the center of the LED board.

Waveguide halves 1608 maybe snap fit, adhesively bonded, ultrasonically welded together or otherwise joined together, sandwiching the electrode in between the two waveguide halves. The waveguide halves form a cylindrical shape around the electrode, thereby illuminating around the electrode. The distal portion of the waveguide may include a lens, a plurality of lenslets or other optical features which help shape the light emitted therefrom. In this embodiment, the optical waveguide has an outer surface that is multi-faceted forming a polygon which approximates a cylinder. This extraction surface of the waveguide may be flat or curved or even angled or tapered to provide better light directionality, for example with respect to divergence of the light. Having a plurality of facets allows better mixing of light as it passes through the waveguide. Standoffs 1610 in a channel in each half of waveguide prevent direct contact between the waveguide and the electrode, thereby minimizing contact and subsequent light loss. The channel in each half of the waveguide preferably matches the shape of the electrode which lies therein.

LED board 1606 includes one or more LEDs for providing light which passes through the waveguide. The LED board may be any of the LED or other light sources described in this specification. The LED may also be parabolically shaped to help focus and deliver the light to the waveguide. In some embodiments, the conductor portion of the electrode may pass through the center of the LED board, or the conductor may pass off center through the LED board.

A layer of FEP cladding is disposed over the waveguide and may be heat shrunk down on the two halves, thereby securing the two together. Optionally in conjunction with the FEP cladding or as an alternative to the FEP cladding, other optical coatings may be used in this or any of the embodiments disclosed herein in order to provide a low index of refraction material adjacent the waveguide to prevent or minimize light loss. Also, an air gap may be disposed against the waveguide to help minimize or prevent light loss since the air gap would provide a lower index of refraction adjacent the waveguide. An outer-most aluminum tube 1600 or other heat conductive material, is then disposed over the FEP cladding and helps keep the components together and also serves as a heat sink to remove heat buildup. This tube is coupled to the LED core to dissipate the heat. The entire assembly may then be coupled to a handpiece and it may telescope in or out of the handpiece. A locking mechanism (not shown) such as a collet or quarter turn lock may be used to lock the electrode in position once it has been telescoped into a desired position.

FIG. 16B is an end view of the illuminated energy tip 1602, and FIG. 16C is a cross-section taken along the line B-B in FIG. 16B. FIG. 16C highlights the FEP coated section 1620, as well as the section of electrode 1622 coupled with standoffs 1610 to minimize direct contact between the electrode and the waveguide.

In any of the embodiments described herein, the waveguide may also be a lens or have a lens portion for controlling light delivered from the waveguide. Therefore, the waveguide with or without a lens, or a separate lens may be mounted on or otherwise coupled to the LED light source or illumination element being used. Optionally, and embodiment may therefore include an optical element such as a lens mounted in front of the illumination element such as an LED to direct and shape the light onto the surgical field.

In any of the embodiments described herein, light may be provided to the waveguide by any number of techniques. An illumination element may be disposed in the handle or adjacent a portion of the waveguide. The illumination element may be a single LED or multiple LEDs. The LED or multiple LEDs may provide white light, or any desired color. For example, when multiple LEDs are used, the LEDs may provide different colors such as red, green, or blue (RGB) and therefore the multiple LEDs may be adjusted to provide a desired color of light that is input into the waveguide. Thus, the waveguide becomes more important since it will mix the different colors of light as the light is transmitted along the length of the waveguide, mixing the different colors of light so that a uniform color light is delivered to the target. Multiple colors may be used to provide varying shades of white colored light, or any other desired color which helps the surgeon or operator visualize and distinguish various objects such as tissue in the surgical field. Filters or coatings may be applied to any of the waveguides to filter specific frequencies of energy out.

Alternatively or in combination, the illumination element may be a fiber optic or fiber bundle in any of the embodiments described herein. For example, a fiber optic may input light to the waveguide from an external source such as a xenon lamp. Light from the external source may be transmitted through the fiber optic or fiber optic bundle through a cable, through the handle, and to the proximal end of the waveguide. The fiber optic or fiber optic bundle may be butted up against the waveguide to provide light to the waveguide and subsequently to a surgical field through the waveguide. A lens or other optical element may be used at the distal end of the fiber optic or fiber bundle to input light to the waveguide with desired optical properties. The light source, for example an external lamp box, may be provided outside the surgical field. Alternatively or in combination, the light source may be a light source in the cable connection. Alternatively or in combination, the light source may be provided in a housing coupled to the cable or to any part of the device.

In any of the embodiments, the waveguide may be made out of a material which has desired optical and mechanical properties. Exemplary materials include acrylic, polycarbonate, cyclo olefin polymer or cyclo olefin copolymer. Additionally malleable silicones may be used to form the waveguide so that they may be shaped (plastically deformed) into a desired configuration. Moldable Silicone can also be coupled directly to the energy tip to provide a waveguide coupled to the tip and that flexes with the tip when the tip is bent or otherwise flexed. Manufacturers such as Dow Corning and Nusil produce moldable silicones which may be used to form the waveguide.

Additionally, in any of the embodiments described herein, sensors may be integrated into the waveguide or energy tip. These sensors include but are not limited to image sensors such as CMOS or CCD sensors. Sensors could also be thermal or fiber optic to collect spectroscopic information. Sensors may be disposed or otherwise integrated into the handle.

Figure 16D:
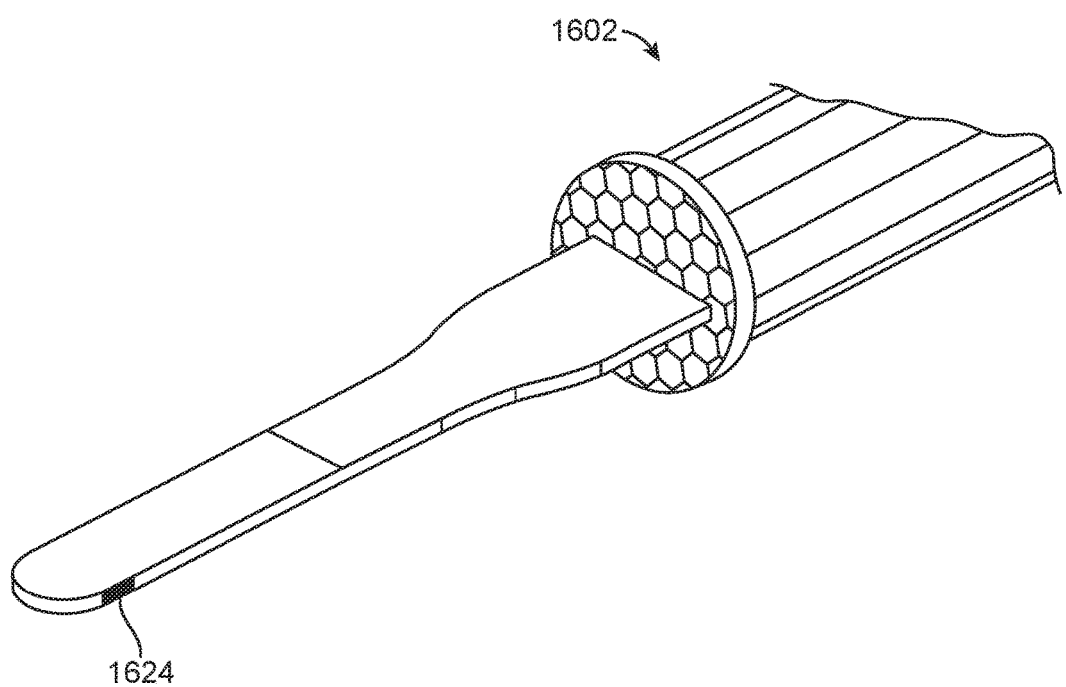

The tip may also include means for sensing to actively measure inductance of the tissue in the surgical field. Knowing the inductance of the tissue allows warning the user if the tip is about to cut through or otherwise damage critical structures. It is also contemplated integrating fiber sensing into the tip to measure temperature spread of the tissue as well as to perform spectroscopic analysis of the tissue. Still other embodiments may include an imaging element such as a camera that can be mounted on the pencil handle or integrated into the sleeve or other portions of the electrosurgical tip. Any of these features may be used or combined with the illuminated tip. FIG. 16D shows an exemplary embodiment of an energy tip 1602 with sensor 1624 integrated therein. The sensor 1624 may for example be an optical sensor, thermal sensor, inductance sensor, or spectroscopic sensor. Only one sensor is represented herein, however it will be understood that any number or combination of sensors may be integrated into one or more of the energy tip, waveguide, handle, or combinations thereof.

Still other embodiments may include handle that has venting features which allow air to circulate through the handle, thereby facilitating cooling of the handle and waveguide.

Figure 17A:
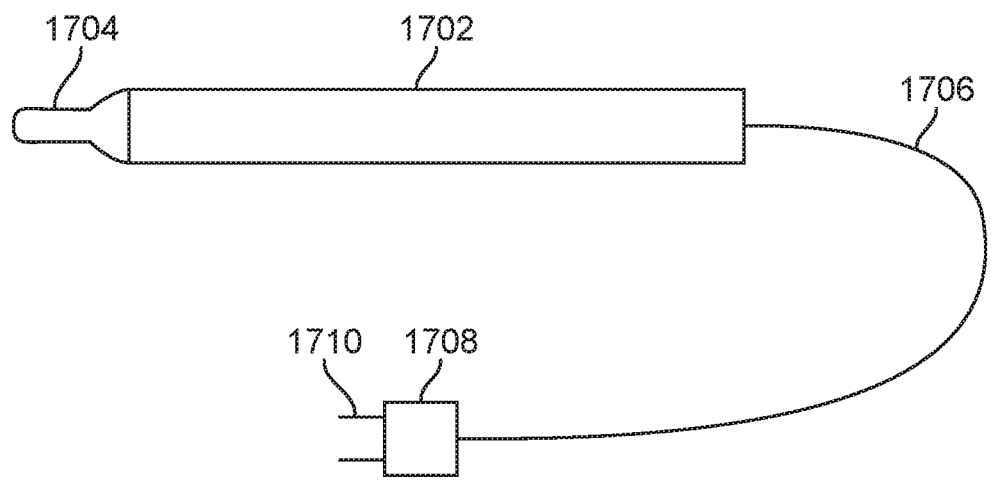
FIGS. 17A-17B illustrate an optional battery feature.
Figure 17B:
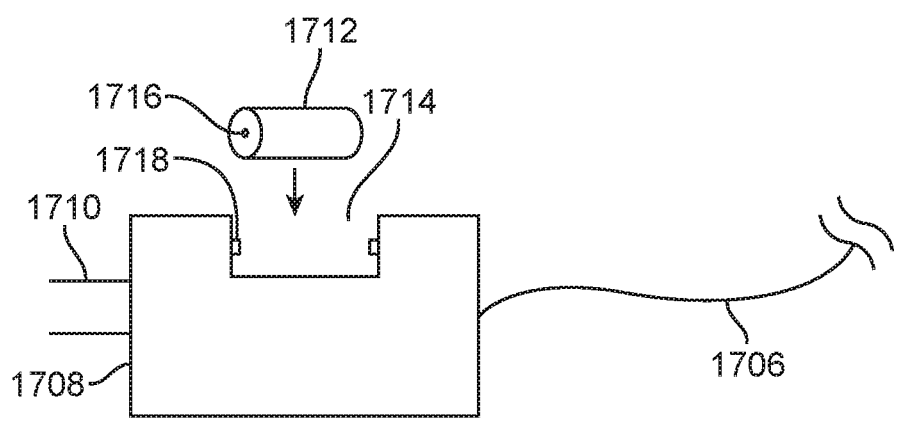

FIGS. 17A-17B illustrate use of an optional battery or other power source that provides energy to the illumination element. This optional feature may be used in any of the embodiments described herein.

FIG. 17A illustrates an electrosurgical instrument having a pencil or handle 1702 with an electrode 1704 with or without illumination element coupled to the distal portion of the handle. An instrument cable 1706 is fixedly or releasably coupled to the proximal portion of the handle, and the opposite end of the cable 1706 includes a plug or adapter or connector 1708 with electrical connector prongs 1710 for coupling with the electrosurgical generator or any other external box (e.g. controller, light source, power source, etc.).

FIG. 17B highlights features of the plug 1708 which includes a recessed region 1714 that is sized and shaped to receive a battery 1712 or other power source (e.g. capacitor) that can be used to provide power to the illumination element (e.g. a LED). Contacts on the battery 1716 engage corresponding contacts 1718 in the recessed region 1714 to complete the electrical circuit. The battery may be a disposable battery or a rechargeable battery. This feature allows a battery to be easily replaced during surgery without interrupting a surgeon who may be using the electrosurgical instrument. Also, this portion of the plug is typically outside of the sterile field thereby further facilitating its replacement. The end of the cable 1706 coupled to the plug 1708 may be fixedly or releasably attached to the plug. Thus, the plug may be easily swapped with a new plug having a fresh battery if needed, further facilitating the procedure.

FIGS. 18A-18E illustrate still another exemplary embodiment of an illuminated electrosurgical tip 1802. One of skill in the art will appreciate that any of the features described in this embodiment may be used in conjunction with, or substituted for features in any of the other embodiments described herein.

Figure 18A:
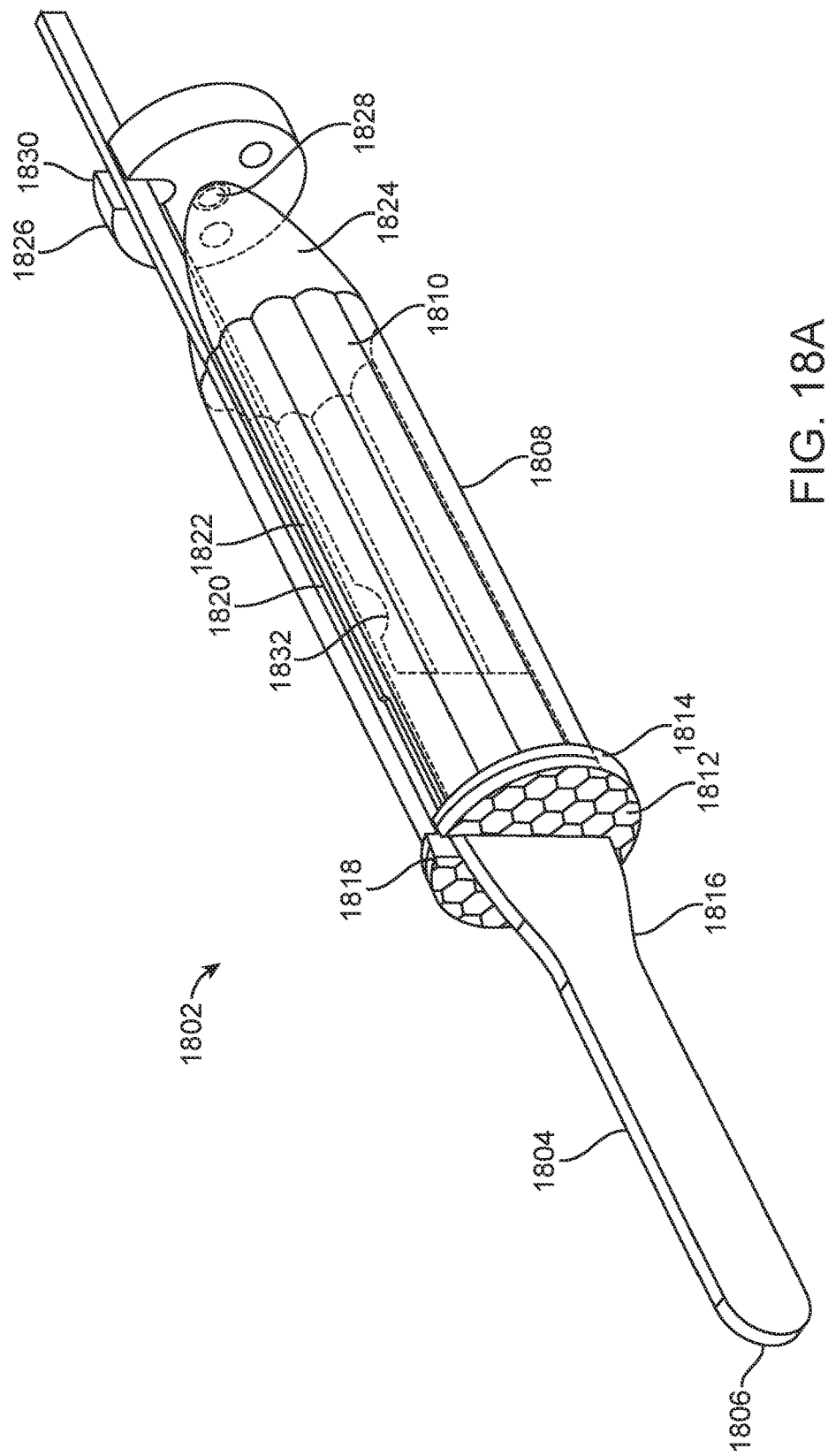
FIGS. 18A-18F illustrate another exemplary embodiment of an illuminated energy tip.
Figure 18B:
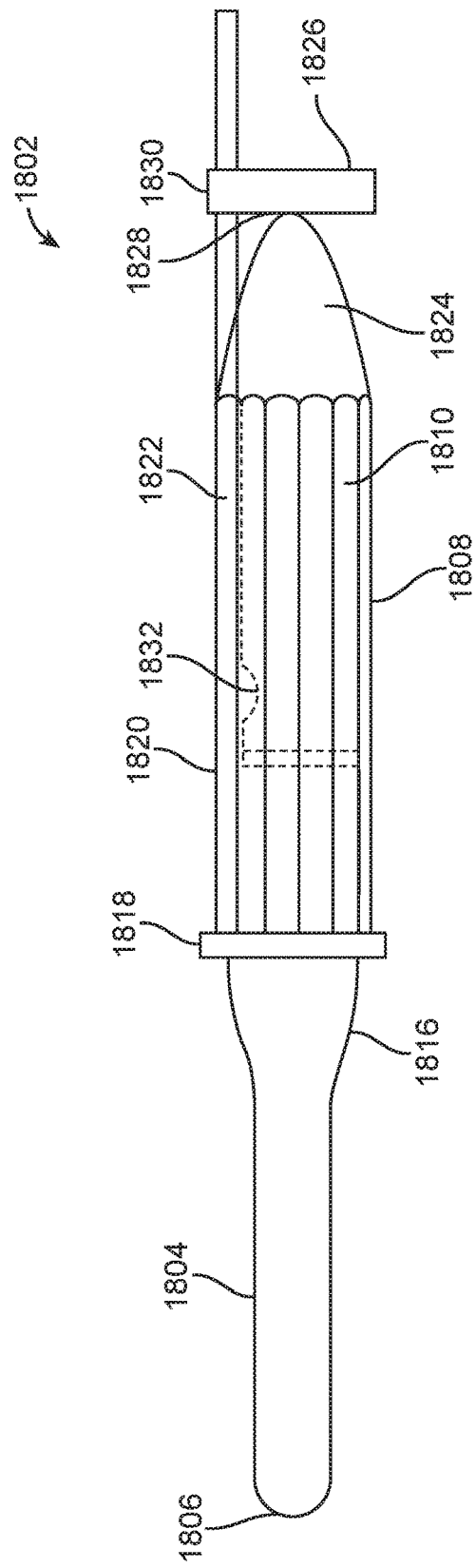

FIG. 18A illustrates illuminated electrosurgical tip 1802 having an electrode tip 1804 coupled to a waveguide 1808 and having an illumination element 1828 on a circuit board 1826 adjacent a proximal end of the waveguide. The electrode tip 1804 has a distal rounded tip 1806 and may have an insulated and uninsulated area similar to that previously described in other embodiments to control delivery of energy to target tissue. The electrode tip 1804 flares outwardly 1816 (or tapers distally) into a flat planar section which then terminates and only an elongate arm 1820 extends proximally. The elongate arm 1820 is used as a conductor to deliver energy from an energy source to the electrode tip. The waveguide has a narrow vertically oriented slit 1818 which then transitions into an elongate channel 1822 for receiving the flat planar section and the elongate arm. A rounded protrusion 1832 (best seen in FIG. 18B) extends from the elongate arm and is received in a correspondingly shaped recess in the waveguide and prevents axial movement of the electrode relative to the waveguide.

The waveguide is preferably a non-fiber optic optical waveguide formed as a single integral piece such as by injection molding. The distal portion of the waveguide includes a plurality of microstructures 1812 for controlling the light extracted therefrom and ensuring that the extracted light has desired optical properties (e.g. divergence, intensity, etc.). A rim 1814 is formed around the microstructures and serves as a surface against which the inner surface of metal tube may lie against. The metal tube has been previously described above and serves as a heat sink. The body of the waveguide is preferably multi-faceted with a series of outer planar surfaces forming a polygonal outer surface. This helps with light transmission through the waveguide as the multiple surfaces allow light to bounce off multiple surfaces, thereby providing more mixing of light.

The proximal end of the waveguide is preferably parabolically shaped in order to help guide light into the waveguide from the illumination element 1828 which is preferably an LED. The parabola is centered over the LED. Arm 1820 is offset from the central axis of the waveguide and is received in a slot 1830 in circuit board 1826.

Figure 18C:
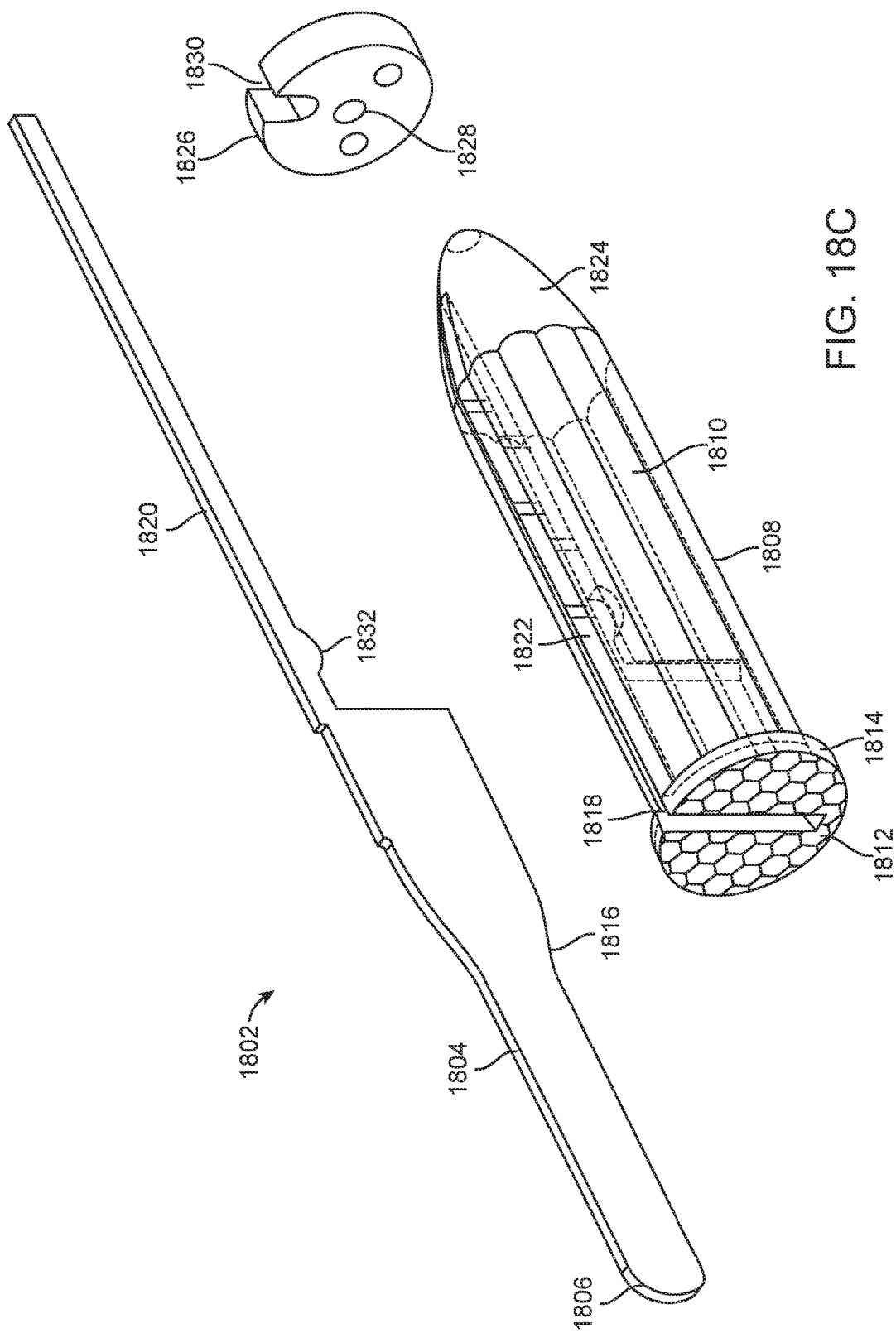
Figure 18D:
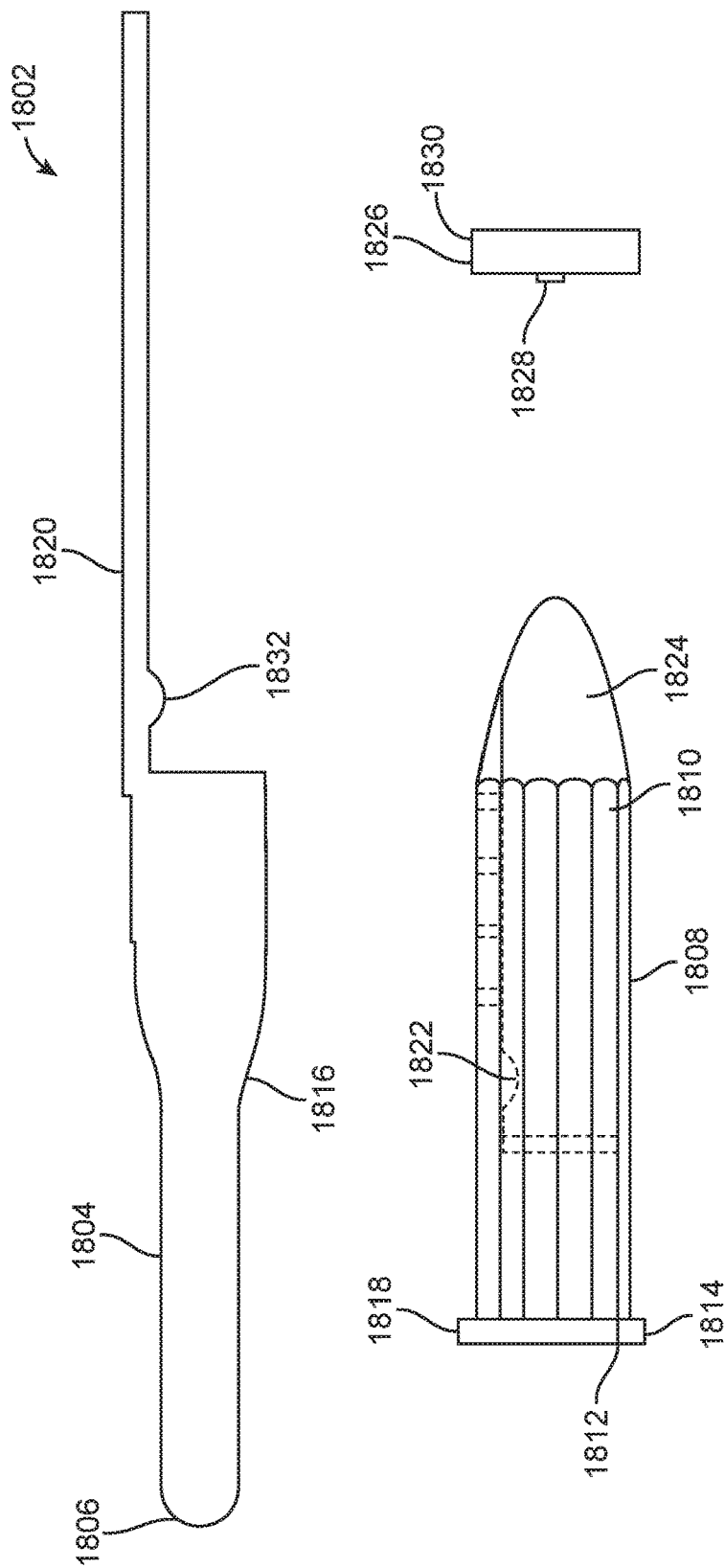

FIG. 18C illustrates an exploded view of the illuminated electrode tip 1802, while FIG. 18D shows an exploded side view of the illuminated electrode tip 1802.

Figure 18E:
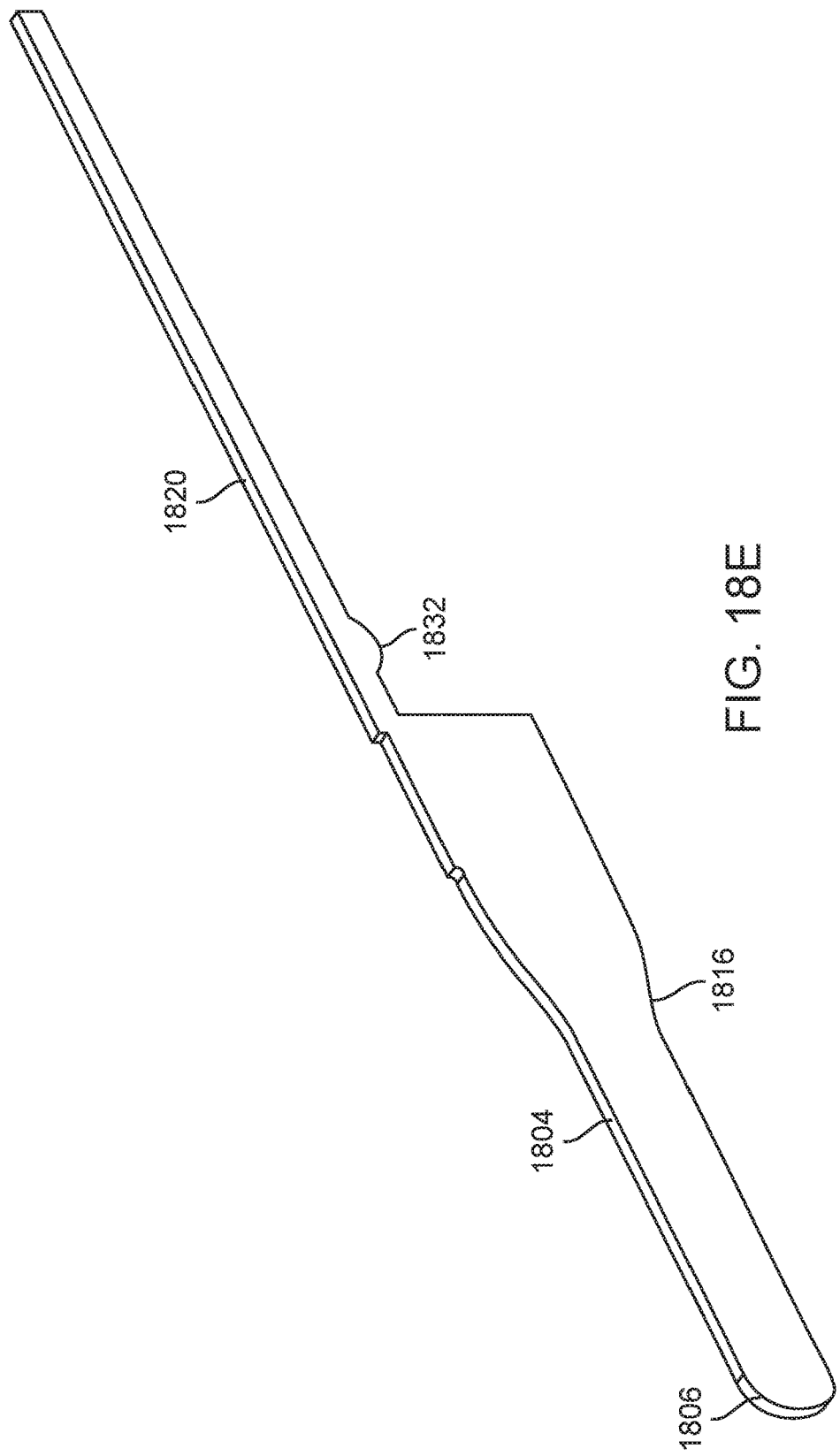
Figure 18F:
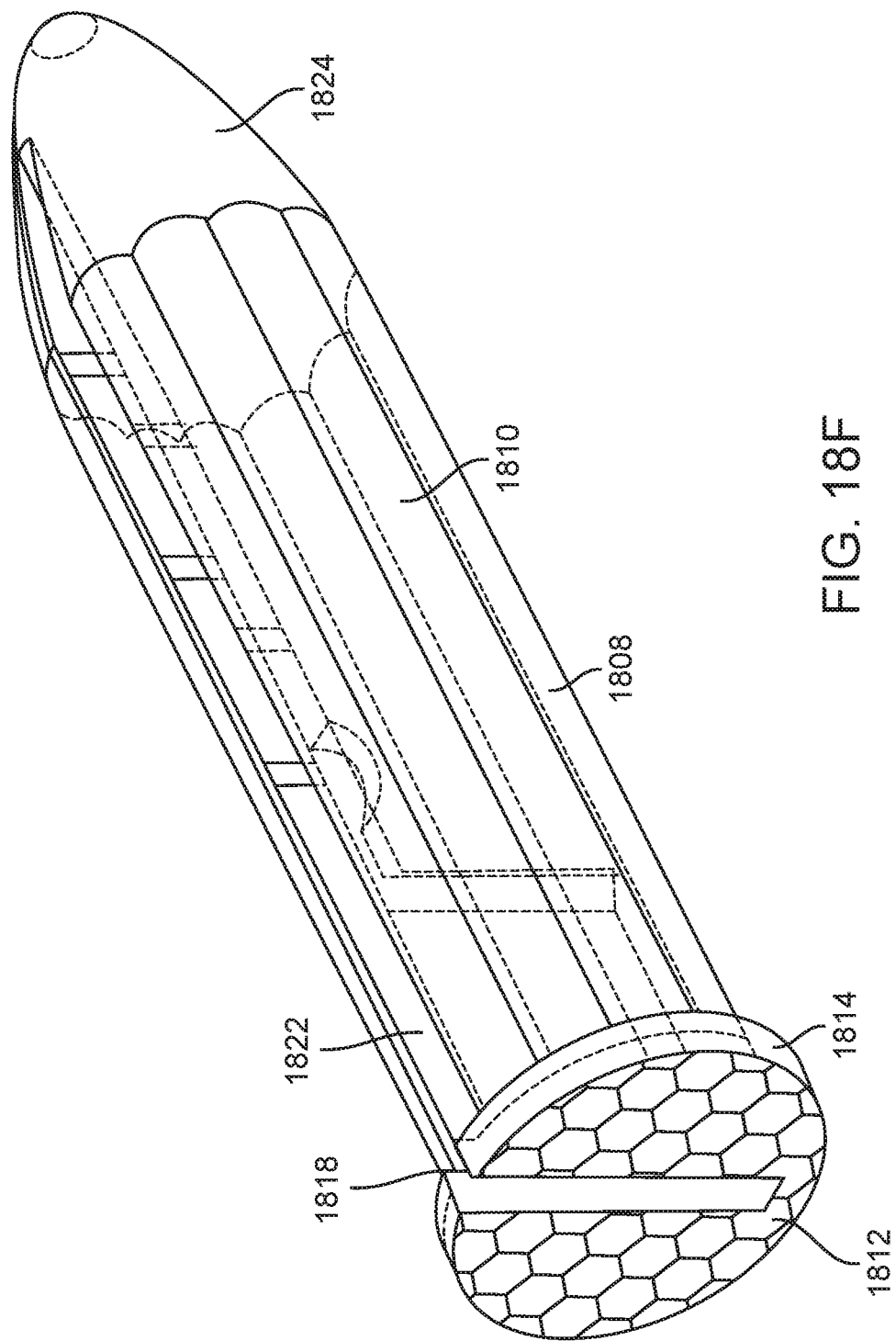

FIG. 18E illustrates a perspective of the electrode 1804 and FIG. 18F shows a perspective view of the waveguide 1808.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An illuminated electrosurgical instrument, said instrument comprising:
    a handle having a proximal end and a distal end;
    a non-fiber optic optical waveguide having a proximal end and a distal end, wherein the optical waveguide is adjustably coupled to the handle such that a distance between the distal end of the optical waveguide and the proximal end of the handle is adjustable without decoupling the optical waveguide from the handle;
    a locking mechanism selected from the group consisting of a collet, a twist-lock, a quarter-turn lock, and a protrusion-recess locking pair, wherein the locking mechanism is coupled to the optical waveguide for selectively locking the optical waveguide in a given position relative to the proximal end of the handle;
    an illumination element configured to generate light and coupled to the proximal end of the optical waveguide; and
    an electrosurgical tip coupled to the optical waveguide, wherein the illumination element and the electrosurgical tip are configured to move with the optical waveguide as the optical waveguide is adjusted relative to the handle.

2. The illuminated electrosurgical instrument of claim 1, wherein the electrosurgical tip is removably coupled with the optical waveguide.

3. The illuminated electrosurgical instrument of claim 1, wherein the electrosurgical tip is integrally formed with the optical waveguide.

4. The illuminated electrosurgical instrument of claim 1, wherein the electrosurgical tip is flat, curved, tapered, or combinations thereof.

5. The illuminated electrosurgical instrument of claim 1, wherein the electrosurgical tip comprises an electrode.

6. The illuminated electrosurgical instrument of claim 1, wherein the optical waveguide comprises one or more of acrylic, polycarbonate, cyclo-olefin polymer, cyclo-olefin copolymer, or malleable silicones.

7. The illuminated electrosurgical instrument of claim 1, wherein the optical waveguide is tapered at the proximal end such that a cross-sectional area of the proximal end of the optical waveguide is smaller than a cross-sectional area of the distal end of the optical waveguide.

8. The illuminated electrosurgical instrument of claim 1, wherein the optical waveguide comprises a light extraction surface through which light is extracted from the optical waveguide, the light extraction surface tapered.

9. The illuminated electrosurgical instrument of claim 1, wherein the optical waveguide comprises a plurality of flat planar facets forming a polygonal outer surface.

10. The illuminated electrosurgical instrument of claim 1, wherein the illumination element comprises at least one light emitting diode (LED), a xenon lamp, or a combination thereof.

11. The illuminated electrosurgical instrument of claim 1, wherein the illumination element is in the handle.

12. The illuminated electrosurgical instrument of claim 1, wherein the illumination element is external to the handle.

13. The illuminated electrosurgical instrument of claim 1, wherein the optical waveguide has a central lumen at least partially housing a proximal portion of the electrosurgical tip such that the proximal portion of the electrosurgical tip fully occupies the lumen.

14. The illuminated electrosurgical instrument of claim 1, further comprising a conducting element disposed on or around the optical waveguide and coupled to the electrosurgical tip, and wherein the optical waveguide is a solid rod.

15. The illuminated electrosurgical instrument of claim 1, wherein the optical waveguide has a central lumen at least partially housing a conducting element which fully occupies the lumen, the conducting element selected from a group consisting of comprises a wire, a rod, and a tube.

16. The illuminated electrosurgical instrument of claim 1, further comprising one or more sensors selected from the group consisting of an image sensor, a thermal sensor, and an inductance sensor.

17. The illuminated electrosurgical instrument of claim 13, further comprising an optical cladding directly coupled to one or more of an outer surface of the optical waveguide or the central lumen of the optical waveguide.

18. The illuminated electrosurgical instrument of claim 1, wherein the locking mechanism comprises the collet,
    wherein the collet comprises a nose piece and a base piece, and wherein the base piece of the collet has a hollow inner diameter, which has (i) a split tapered end and (ii) is sized to receive the optical waveguide.

19. The illuminated electrosurgical instrument of claim 18, further comprising at least two protrusions on an outer diameter of the base piece, wherein the at least two protrusions are configured to mate with two internal helix grooves on the nose piece.

20. The illuminated electrosurgical instrument of claim 19, wherein the nose piece and the base piece have interfering tapers such that tightening the nose piece against the base piece causes the collet to apply in an inward radial force on the optical waveguide, wherein the inward radial force clamps the optical waveguide in a fixed position relative to the handle.

21. The illuminated electrosurgical instrument of claim 1, wherein the optical waveguide has a concave cutout extending between the proximal end and the distal end of the optical waveguide,
wherein a conductor element is in the concave cutout, and
wherein the conductor element is electrically connected to the electrosurgical tip.

22. The illuminated electrosurgical instrument of claim 21, wherein the conductor element is shaped to complement the concave cutout such that the optical waveguide and the conductor element cooperatively form a cylinder having a circular cross-section.

23. The illuminated electrosurgical instrument of claim 1, further comprising an image sensor optically coupled with the optical waveguide.

24. The illuminated electrosurgical instrument of claim 1, further comprising a sensor integrated with the electrosurgical tip, said sensor selected from the group consisting of thermal sensor and inductance sensor.

25. The illuminated electrosurgical instrument of claim 1, further comprising a metal tube surrounding and thermally coupled with the optical waveguide for dissipating heat generated therefrom.

26. The illuminated electrosurgical instrument of claim 1, further comprising:
a conductive element having one or more first electrical conductors coupled to the illumination element and one or more second electrical conductor coupled to the electrosurgical tip;
a plug comprising a plurality of electrical connector prongs coupled to the one or more second electrical conductors, wherein the plug comprises a recess; and
a battery received in the recess of the plug and coupled to the one or more first electrical conductors.

27. An illuminated electrosurgical instrument, said instrument comprising:
a handle having a proximal end and a distal end;
a non-fiber optic optical waveguide having a proximal end and a distal end, wherein the optical waveguide is adjustably coupled to the handle such that a distance between the distal end of the optical waveguide and the proximal end of the handle is adjustable without decoupling the optical waveguide from the handle;
an illumination element configured to generate light and coupled to the proximal end of the optical waveguide; and
an electrosurgical tip coupled to the optical waveguide,
wherein the illumination element and the electrosurgical tip are configured to move with the optical waveguide as the optical waveguide is adjusted relative to the handle, and
wherein the optical waveguide comprises one or more smoke evacuation channels extending axially through the optical waveguide to the proximal end of the optical waveguide.

28. An illuminated electrosurgical instrument, said instrument comprising:
a handle having a proximal end and a distal end;
a non-fiber optic optical waveguide having a proximal end and a distal end, wherein the optical waveguide is adjustably coupled to the handle such that a distance between the distal end of the optical waveguide and the proximal end of the handle is adjustable without decoupling the optical waveguide from the handle, wherein the optical waveguide is telescopically arranged with the handle such that (i) a portion of the optical waveguide telescopes out of the handle when the optical waveguide is adjusted distally relative to the handle and (ii) the portion of the optical waveguide telescopes into the handle when the optical waveguide is adjusted proximally relative to the handle;
an illumination element configured to generate light, wherein the illumination element is coupled to the proximal end of the optical waveguide, wherein the illumination element is proximal of the proximal end of the handle; and
an electrosurgical tip coupled to the optical waveguide and comprising an electrode blade, wherein a distal portion of the electrode blade is covered by an insulator coating.

29. The illuminated electrosurgical instrument of claim 28, wherein the optical waveguide is independently movable relative to the electrosurgical tip.

30. The illuminated electrosurgical instrument of claim 28, wherein the electrosurgical tip is coupled to the optical waveguide such that movement of the optical waveguide relative the handle results in a corresponding movement of the electrosurgical tip relative to the handle.

31. The illuminated electrosurgical instrument of claim 28, wherein the optical waveguide and the electrosurgical tip are configured to rotate together relative to the handle.

32. The illuminated electrosurgical instrument of claim 28, further comprising a locking mechanism coupled to the optical waveguide and configured to selectively lock the optical waveguide in a given position relative to the proximal end of the handle.

33. The illuminated electrosurgical instrument of claim 28, wherein the electrosurgical tip is removably coupled with the optical waveguide.

* * * * *